US012767731B2

(12) United States Patent
Owen et al.

(10) Patent No.: US 12,767,731 B2
(45) Date of Patent: Oct. 20, 2026

(54) ANTI-IgE ANTIBODY THERAPY FOR MULTIPLE FOOD ALLERGIES

(71) Applicants: Genentech, Inc., South San Francisco, CA (US); Novartis AG, Basel (CH)

(72) Inventors: Ryan Patrick Owen, Millbrae, CA (US); Ahmar Iqbal, San Bruno, CA (US); Robert A. Wood, Lutherville, MD (US)

(73) Assignees: Genentech, Inc., South San Francisco, CA (US); Novartis AG, Basel (CH)

( * ) Notice: Subject to any disclaimer, the term of this patent is extended or adjusted under 35 U.S.C. 154(b) by 0 days.

(21) Appl. No.: 19/331,731

(22) Filed: Sep. 17, 2025

(65) Prior Publication Data

US 2026/0167743 A1 Jun. 18, 2026

Related U.S. Application Data

(63) Continuation of application No. 19/050,002, filed on Feb. 10, 2025, now Pat. No. 12,492,265, which is a continuation of application No. 18/735,125, filed on Jun. 5, 2024, now abandoned, which is a continuation of application No. 18/486,053, filed on Oct. 12, 2023, now Pat. No. 12,030,959, which is a continuation of application No. PCT/US2023/070639, filed on Jul. 20, 2023.

(60) Provisional application No. 63/512,051, filed on Jul. 5, 2023.

(51) Int. Cl.

| | |
|---|---|
| ***C07K 16/42*** | (2006.01) |
| ***A61P 37/08*** | (2006.01) |
| *A61K 39/00* | (2006.01) |

(52) U.S. Cl.

CPC .......... *C07K 16/4291* (2013.01); *A61P 37/08* (2018.01); *A61K 2039/545* (2013.01)

(58) Field of Classification Search

None

See application file for complete search history.

(56) References Cited

U.S. PATENT DOCUMENTS

| | | | | |
|---|---|---|---|---|
| 6,172,213 | B1 | 1/2001 | Lowman | |
| 8,961,964 | B2 * | 2/2015 | Liu | A61P 37/06 424/130.1 |
| 10,034,940 | B2 * | 7/2018 | Liu | A61P 11/02 |
| 10,166,293 | B2 | 1/2019 | Liu et al. | |
| 10,370,456 | B2 | 8/2019 | Winter | |
| 11,767,370 | B2 | 9/2023 | Winter | |
| 12,030,959 | B1 * | 7/2024 | Owen | A61P 37/08 |
| 12,371,510 | B2 | 7/2025 | Winter | |
| 12,492,265 | B2 * | 12/2025 | Owen | A61P 37/08 |
| 2005/0031609 | A1 | 2/2005 | Hultsch et al. | |
| 2008/0206237 | A1 | 8/2008 | Owen et al. | |
| 2021/0095050 | A1 | 4/2021 | Winter | |
| 2023/0227582 | A1 | 7/2023 | Ivan et al. | |
| 2025/0011474 | A1 | 1/2025 | Owen et al. | |
| 2025/0179216 | A1 | 6/2025 | Owen et al. | |
| 2026/0167744 | A1 | 6/2026 | Owen et al. | |

FOREIGN PATENT DOCUMENTS

| | | | |
|---|---|---|---|
| WO | 2021255621 | A1 | 12/2021 |
| WO | 2023111811 | A1 | 6/2023 |
| WO | 2025010085 | A1 | 1/2025 |
| WO | 2025010086 | A1 | 1/2025 |

OTHER PUBLICATIONS

Wood et al., J Allergy Clin Immunol Glob, Jul. 21, 2022;1(4):225-232. doi: 10.1016/j.jacig.2022.05.006. eCollection Nov. 2022. PMID: 37779534.*

Supplemental online material for Wood et al., J Allergy Clin Immunol Glob. Jul. 21, 2022;1(4):225-232., 9 pages.*

Abdel-Gadir, A. et al. (2018, e-pub. May 29, 2018). "Oral Immunotherapy with Omalizumab Reverses the Th2 Cell-Like Program of Regulatory T Cells and Restores Their Function," Clin. Exp. Allergy 48(7):825-836, plus supplemental materials, 35 pages.

Alba Jorda, J.P. et al. (2019). "Omalizumab in Spontaneous Food Tolerance in Adult Patients," Allergy, Abstract #OA0198, 1 page.

Amrol, D. (2010). "Anti-Immunoglobulin E in the Treatment of Refractory Atopic Dermatitis," South Med. J. 103:554-558.

Andorf, S. et al. (2017). "Observational Long-Term Follow-Up Study of Rapid Food Oral Immunotherapy with Omalizumab," Allergy Asthma Clin. Immunol. 13:51, 8 pages.

Andorf, S. et al. (2019, e-pub. Jan. 21, 2019). "A Phase 2 Randomized Controlled Multisite Study Using Omalizumab-Facilitated Rapid Desensitization to Test Continued vs Discontinued Dosing in Multifood Allergic Individuals," EClinicalMedicine 7:27-38, plus supplemental materials, 77 pages.

Andorf, S. et al. (2018). "Anti-IgE Treatment with Oral Immunotherapy in Multifood Allergic Participants: Results of a Randomized, Double-blinded Control Trial," Lancet Gastroenterol Hepatol. 3(2):85-94, 26 pages.

Arasi, S. et al. (2020). "Abstract 1650—Impact of Omalizumab on Severe Food Allergy in 54 Italian Patients with Concomitant Asthma: 6-Year-Long Experience," European Journal of Allergy and Clinical Immunology, 1 page.

Arasi, S. et al. (2020). "Role of In Vitro Testing in Food Allergy," Pediatr Allergy Immunol. 31(Suppl 26):36-38.

(Continued)

*Primary Examiner* — Michael Szperka

(74) *Attorney, Agent, or Firm* — Morrison & Foerster LLP

(57) ABSTRACT

The present disclosure provides methods and kits for treating or preventing an allergic reaction to a food allergen consumed by a human subject with one or more food allergies. In particular, the present disclosure provides prophylactic therapies comprising administration of an anti-IgE antibody at a specific dose to a human subject who is allergic to one or more food allergens.

29 Claims, 2 Drawing Sheets

Specification includes a Sequence Listing.

(56) References Cited

OTHER PUBLICATIONS

Arasi, S. et al. (2021). "Omalizumab as Monotherapy for Food Allergy," Curr. Opin. Allergy Clin. Immunol. 21(3):286-291.
Arm, J.P. et al. (2014). "Pharmacokinetics, Pharmacodynamics and Safety of QGE031 (ligelizumab), A Novel High-Affinity Anti-IgE Antibody, in Atopic Subjects," Clin. Exp. Allergy, 44:1371-1385, with supplementary materials, 36 pages.
Azzano, P. et al., (2021, e-pub. Sep. 24, 2020). "Determinants of Omalizumab Dose-Related Efficacy in Oral Immunotherapy: Evidence from a Cohort of 181 Patients," J. Allergy Clin. Immunol. 147(1):233-243.
Barni, S. et al. (2020). "Immunoglobulin E (IgE)-Mediated Food Allergy in Children: Epidemiology, Pathogenesis, Diagnosis, Prevention, and Management," Medicina, 56:111, 16 pages.
Barrios, J.L. et al. (2011). "Efficacy of Omalizumab Therapy in a Case of Severe Atopic Dermatitis," Allergy Asthma Clin. Immunol. 7(Suppl. 2):A33, 1 page.
Bedoret, D. et al. (2012). "Changes in Antigen-Specific T-Cell Number and Function During Oral Desensitization in Cow's Milk Allergy Enabled with Omalizumab," Controlled Clinical Trial, Mucosal Immunol. 5(3):267-276, 23 pages.
Belloni, B. et al. (2007, e-pub. Oct. 15, 2007). "Low-Dose Anti-IgE Therapy in Patients with Atopic Eczema with High Serum IgE Levels," J. Allergy Clin. Immunol. 120(5):1223-1225.
Björkander, S. et al. (2022, e-pub. Oct. 31, 2021). "Transcriptome Changes During Peanut Oral Immunotherapy and Omalizumab Treatment," Pediatr. Allergy Immunol. 33(1):e13682, 5 pages.
Boyce, J.A. (2006, e-pub. May 10, 2006). "Successful Treatment of Cold-Induced Urticaria/Anaphylaxis with Anti-IgE," J. Allergy Clin. Immunol. 117(6):1415-1418.
Bozoghlanian, V. et al. (2017). "Efficacy of Omalizumab in Reducing Food Allergy," J. Allergy Clin. Immunol. 139(2):AB135, Abstract # 432, 1 page.
Brandström, J. et al. (2017, e-pub. Jan. 10, 2017). "Individually Dosed Omalizumab: An Effective Treatment for Severe Peanut Allergy," Clin. Exp. Allergy 47(4):540-550.
Brandström, J. et al. (2019, e-pub. Aug. 15, 2019). "Individually Dosed Omalizumab Facilitates Peanut Oral Immunotherapy in Peanut Allergic Adolescents," Clin. Exp. Allergy 49(10):1328-1341.
Brough, H.A. et al. (2020). "Defining Challenge-Proven Coexistent Nut and Sesame Seed Allergy: A Prospective Multicenter European Study," J. Allergy Clin. Immunol. 145(4):1231-1239.
Burk, C.M. et al. (2017, e-pub. Dec. 22, 2016). "Eosinophilic Esophagitis During Peanut Oral Immunotherapy with Omalizumab," J. Allergy Clin. Immunol. Pract. 5(2):498-501.
Burks, A.W. et al. (2012). "Oral Immunotherapy for Treatment of Egg Allergy in Children," N. Engl. J. Med. 3673:233-243.
Busse, W. et al. (2001). "Omalizumab, Anti-IgE Recombinant Humanized Monoclonal Antibody, for the Treatment of Severe Allergic Asthma," J. Allergy Clin. Immunol. 108(2):184-190.
Busse, W.W. et al. (2011). "Randomized Trial of Omalizumab (Anti-IgE) for Asthma in Inner-City Children," N. Engl. J. Med. 364:1005-1015.
Bégin, P. et al. (2014). "Phase 1 Results of Safety and Tolerability in a Rush Oral Immunotherapy Protocol to Multiple Foods Using Omalizumab," Allergy, Asthma & Clinical Immunology 10:7, 10 pages.
Caruso, C. et al. (2010). "Omalizumab Efficacy in a Girl with Atopic Eczema," Allergy 65:278-279.
CAS Registry No. 242138-07-4. (Apr. 15, 2023) "Omalizumab," NCBI: 33 pages.
Chang, T.W. et al. (2012). "The Pharmacological Mechanisms of Omalizumab in Patients with Very High IgE Levels—Clues from Studies on Atopic Dermatitis," Dermatologica Sinica 30:147-153.
Chase, N. et al. (Nov. 10-14, 2022). "Improvements in Select Patient-Reported Outcomes are Similar Across Different Omalizumab Dosing Regimens," Poster presented at the American College of Allergy, Asthma & Immunology (ACAAI) 2022 Annual Scientific Meeting, Louisville, KY, 1 page.
Chen, G. et al. (2021). "High-Resolution Epitope Mapping by AllerScan Reveals Relationships Between IgE and IgG Repertoires During Peanut Oral Immunotherapy," Randomized Controlled Trial, Cell Reports Medicine 2(10):100410, 18 pages.
Chinthrajah, R.S. et al. (2022). "Updating the CoFAR Grading Scale for Systemic Allergic Reactions in Food Allergy," J. Allergy Clin. Immunol. 149(6):2166-2170, 13 pages.
Chinuki, Y. et al. (2019). "Efficacy and Safety of Long-Term Anti-IgE Antibody Therapy in Adult Patients with Wheat Allergy," J. Derm. Nurses' Assoc. 2 pages.
Chinuki, Y. et al. (2023, e-pub. Jan. 12, 2023). "Efficacy and Safety of Omalizumab in Adult Patients with Wheat-Dependent Exercise-Induced Anaphylaxis: Reduction of in vitro Basophil Activation and Allergic Reaction to Wheat," Allergology International 72(3):444-450, plus supplemental materials, 16 pages.
Clinicaltrials NCT00086606 (First Posted Jul. 9, 2004). "A Safety and Efficacy Study of Xolair in Peanut Allergy," 7 pages.
Clinicaltrials NCT00382148 (First Posted Sep. 28, 2006). "A Study of Xolair in Peanut-Allergic Subjects Previously Enrolled in Study Q2788g," 8 pages.
Clinicaltrials NCT00932282 (First Posted Jul. 3, 2009). "Peanut Oral Immunotherapy and Anti-Immunoglobulin E (IgE) for Peanut Allergy (PAIE/Xolair)," 10 pages.
Clinicaltrials NCT00968110 (First Posted Aug. 28, 2009). "Xolair Treatment for Milk Allergic Children," 8 pages.
Clinicaltrials NCT01157117 (First Posted Jul. 5, 2010). "OIT and Xolair® (Omalizumab) in Cow's Milk Allergy," 13 pages.
Clinicaltrials NCT01290913 (First Posted Feb. 7, 2011). "Xolair Enhances Oral Desensitization in Peanut Allergic Patients," 8 pages.
Clinicaltrials NCT01510626 (First Posted Jan. 16, 2012). "Omalizumab With Oral Food Immunotherapy with Food Allergies Open Label Safety Study in a Single Center," 7 pages.
Clinicaltrials NCT01781637 (First Posted Feb. 1, 2013). "Peanut Reactivity Reduced by Oral Tolerance in an Anti-IgE Clinical Trial (PRROTECT)," 8 pages.
Clinicaltrials NCT02402231 (First Posted Mar. 30, 2015). "Treatment of Severe Peanut Allergy With Xolair (Omalizumab) and Oral Immunotherapy (FASTX)," 7 pages.
Clinicaltrials NCT02570984 (First Posted Oct. 8, 2015). "Preventing Asthma in High Risk Kids (PARK)," 9 pages.
Clinicaltrials NCT02626611 (First Posted Dec. 10, 2015). "Multi Immunotherapy to Test Tolerance and Xolair (M-TAX)," 11 pages.
Clinicaltrials NCT02643862 (First Posted Dec. 31, 2015). "Study Using Xolair in Rush Multi Oral Immunotherapy in Multi Food Allergic Patients (MAP-X)," 10 pages.
Clinicaltrials NCT02879006 (First Posted Aug. 25, 2016). "E-B-FAHF-2, Multi OIT and Xolair (Omalizumab) for Food Allergy," 9 pages.
Clinicaltrials NCT03181009 (First Posted Jun. 8, 2017). "Multi OIT to Test Immune Markers After Minimum Maintenance Dose," 10 pages.
Clinicaltrials NCT03679676 (First Posted Sep. 20, 2018). "Clinical Study Using Biologics to Improve Multi OIT Outcomes (COMBINE)," 11 pages.
Clinicaltrials NCT03881696 (First Posted Mar. 19, 2019). "Omalizumab as Monotherapy and as Adjunct Therapy to Multi-Allergen OIT in Food Allergic Participants (OUtMatch)," 40 pages.
Clinicaltrials NCT04037176 (First Posted Jul. 30, 2019). "Behandling af Boern Med Foedevareallergi Med Omalizumab (Xolair)," 10 pages.
Clinicaltrials NCT04045301 (First Posted Aug. 5, 2019). "Omalizumab to Accelerate a Symptom-driven Multi-food OIT (BOOM)," 10 pages.
Consortium for Food Allergy Research (Feb. 23, 2023). NIAID Site Search results for CoFAR-11, retrieved from the internet: https://www.niaid.nih.gov/search?search=cofar-11, last visited on Dec. 5, 2023, 2 pages.
Consortium for Food Allergy Research (Feb. 23, 2023). "Protocol CoFAR-11 Omalizumab as Monotherapy and as Adjunct Therapy to Multi-Allergen OIT in Food Allergic Children and Adults OUtMATCH", Version 6.0 dated Jun. 13, 2022, retrieved from the Internet on Sep. 15, 2023, https://www.niaid.nih.gov/sites/default/files/cofar-11-outmatch-protocol.pdf, 157 pages.

(56) References Cited

OTHER PUBLICATIONS

Crespo, J.B. et al. (2021). "Real Life Study of the Use of Omalizumab for Pediatric Patients with Multiple Food Allergies," Allergol Immunopathol (Madr) 49(2):15-22.
Dantzer, J.A. et al. (2021). "Omalizumab as an Adjuvant in Food Allergen Immunotherapy," Curr. Opin. Allergy Clin. Immunol., 21:278-285.
Dantzer, J.A. et al. (2021). "Update on Omalizumab in Allergen Immunotherapy," Curr. Opin. Allergy Clin. Immunol., 21:559-568.
Dantzer, J.A. et al. (2022). "Treatment for Food Allergy: Current Status and Unmet Needs," J. Allergy Clin. Immunol., pp. 1-14.
Dantzer, J.A. et al. (2023). "Anti-Immunoglobulin E for Food Allergy," Ann. Allergy Asthma Immunol. 000:1-11.
De Silva, D. et al. (2022). "Systematic Review of Monotherapy with Biologicals for Children and Adults with IgE-Mediated Food Allergy," Clin. Transi. Allergy e12123, 7 pages.
Do, L.T. et al. (2007). "Atopic Dermatitis: A Review and Evaluation of Treatment with Omalizumab," CML Dermatiol 12:63-70.
FDA. (Jul. 2016). "Prescribing Information for Xolair®," FDA Prescribing Information, 27 pages.
Ferrer, M. et al. (2011, e-pub. Feb. 11, 2011). "Omalizumab is Effective in Non-Autoimmune Urticaria," J. Allergy Clin. Immunol. 127(5):1300-1302.
Fiocchi, A. et al. (2019, e-pub. Feb. 20, 2019). "Impact of Omalizumab on Food Allergy in Patients Treated for Asthma: A Real-Life Study," J. Allergy Clin. Immunol. Pract. 7:1901-1909, 14 pages.
Fiocchi, A. et al. (2021). "The Use of Biologics in Food Allergy," Clin. Exp. Allergy, 51:1006-1018.
Fleischer, D.M. et al. (2013). "Sublingual Immunotherapy for Peanut Allergy: A Randomized, Double-Blind, Placebo-Controlled Multicenter Trial," J. Allergy Clin. Immunol. 131(1):119-127, 20 pages.
Forman, S.B. et al. (2007). "Success of Omalizumab as Monotherapy in Adult Atopic Dermatitis: Case Report and Discussion of the High-Affinity Immunoglobulin E Receptor, FcepsilonRI," Cutis 80:38-40.
Gauvreau, G.M. et al. (2016, e-pub. Apr. 7, 2016). "Efficacy and Safety of Multiple Doses of QGE031 (ligelizumab) Versus Omalizumab and Placebo in Inhibiting Allergen-Induced Early Asthmatic Responses," J. Allergy Clin. Immunol., 138(4):1051-1059.
Genentech Press Release (Aug. 12, 2018). "FDA Grants Breakthrough Therapy Designation for Xolair (Omalizumab) for Food Allergies," 3 pages.
Gernez, Y. et al. (2011, e-pub. Oct. 25, 2010). "Basophil CD203c Levels are Increased at Baseline and Can be Used to Monitor Omalizumab Treatment in Subjects with Nut Allergy," Int. Arch. Allergy Immunol. 154:318-327.
Groffik, A. et al. (2011). "Omalizumab—An Effective and Safe Treatment of Therapy-Resistant Chronic Spontaneous Urticaria," Allergy 66:303-305.
Gupta, R. et al. (2013, e-pub. Sep. 16, 2013). "The Economic Impact of Childhood Food Allergy in the United States," JAMA Pediatr. 167(11):1026-1031.
Gupta, R.S. et al. (2019). "Prevalence and Severity of Food Allergies Among US Adults," JAMA Network Open 2: e185630, 14 pages.
Hamilton, R.G. et al. (2005, e-pub. Jul. 7, 2005). "Immunological Methods for Quantifying Free and Total Serum IgE Levels in Allergy Patients Receiving Omalizumab (Xolair) Therapy," Journal of Immunological Methods, 303(1-2):81-91.
Heil, P.M. et al. (2010). "Omalizumab Therapy in Atopic Dermatitis: Depletion of IgE Does Not Improve the Clinical Course—A Randomized, Placebo-Controlled and Double Blind Pilot Study," J. Dtsch. Dermatiol Ges. 8:990-998.
Hochhaus, G. et al. (2008, e-pub. Sep. 2008). "Pharmacodynamics of Omalizumab: Implications for Optimized Dosing Strategies and clinical Efficacy in the Treatment of Allergic Asthma," Current Medical Research and Opinion 19(6):491-498.
Hutyrová, B. et al. (2018, e-pub. Jul. 19, 2018). "The Effect of Omalizumab Treatment on Severe Allergic Asthma and Allergic Comorbidities: Real-Life Experience from the Czech Anti-IgE Registry," Adv. Dermatol Allergol. 35(5):510-515.
Ibáñez-Sandin, M.D. et al. (2021). "Oral Immunotherapy in Severe Cow's Milk Allergic Patients Treated with Omalizumab: Real Life Survey from a Spanish Registry," Pediatr. Allergy Immunol. 32:1287-1295.
Incorvaia, C. et al. (2008). "Current and Future Applications of the Anti-IgE Antibody Omalizumab," Biologics: Targets & Therapy 2(1):67-73.
Incorvaia, C. et al. (2008). "Effectiveness of Omalizumab in a Patient with Severe Asthma and Atopic Dermatitis," Monaldi Arch. Chest Dis. 69:78-80.
International Search Report and Written Opinion mailed on Oct. 16, 2023, for PCT Application No. PCT/US2023/070639, filed on Jul. 20, 2023, 13 pages.
International Search Report and Written Opinion mailed on Sep. 27, 2023, for PCT Application No. PCT/US2023/070637, filed on Jul. 20, 2023, 13 pages.
Johansson, S.G.O. et al. (2009). "The Size of the Disease Relevant IgE Antibody Fraction in Relation to 'Total-IgE' Predicts the Efficacy of Anti-IgE (Xolair) Treatment," Allergy, 64:1472-1477.
Jones, J.D. et al. (2008). "Idiopathic Anaphylaxis Successfully Treated with Omalizumab," Ann. Allergy Asthma Immunol. 101:550-551.
Jones, S.M. et al. (2017). "Epicutaneous Immunotherapy for the Treatment of Peanut Allergy in Children and Young Adults," J. Allergy Clin. Immunol. 139(4):1242-1252.e9, 24 pages.
Kanu, A. et al. (2008, e-pub. Nov. 14, 2008). "Treatment of Allergic Bronchopulmonary Aspergillosis (ABPA) in CF with Anti-IgE Antibody (Omalizumab)," Pediatr. Pulmonol. 43:1249-1251.
Kim, H.L. et al. (2010). "Omalizumab: Practical Considerations Regarding the Risk of Anaphylaxis," Asthma-Clin. Immunol. 6:32, 9 pages.
Kopp, M.V. (2011). "Omalizumab: Anti-IgE Therapy in Allergy," Curr. Allergy Asthma Rep. 11:101-106.
Krathen, R.A. et al. (2005). "Failure of Omalizumab for Treatment of Severe Adult Atopic Dermatitis," J. Am. Acad. Dermatol. 53:338-340.
Lafuente, I. et al. (2015). "Possible Recurrence of Symptoms After Discontinuation of Omalizumab in Anti-IgE-Assisted Desensitization to Egg," Pediatric Pulmonology and Allergy 25:714-728.
Lane, J.E. et al. (2006, e-pub. Nov. 25, 2005). "Treatment of Recalcitrant Atopic Dermatitis with Omalizumab," J. Am. Acad. Dermatol. 54(1):68-72.
Langlois, A. et al. (2020). "Protocol for a Double-Blind, Randomized Controlled Trial on the Dose-Related Efficacy of Omalizumab in Multi-Food Oral Immunotherapy," Allergy Asthma Clin. Immunol. 16:25, 16 pages.
Lanier, B. et al. (2009). "Omalizumab for the Treatment of Exacerbations in Children with Inadequately Controlled Allergic (IgE-Mediated) Asthma," J. Allergy Clin. Immunol. 124(6):1210-1216.
Lebecque, P. et al. (2009). "Omalizumab for Treatment of ABPA Exacerbations in CF Patients," Pediatr. Pulmonol. 44:516, 2 pages.
Lee, E.Y. et al. (2021). "Delayed Hypersensitivity Reactions to Multiple Aromatase Inhibitors Followed by Successful Desensitization to Letrozole," Ann. Allergy Asthma Immunol 127:378-397.
Lee, T.H. et al. (2019, e-pub. Jun. 10, 2019). "Peanut Allergy and Oral Immunotherapy," Hong Kong Medical Journal 25(3):228-234.
Leung, D.Y.M. et al. (2003). "Effect of Anti-IgE Therapy in Patients with Peanut Allergy," The New England Journal of Medicine 348:986-993.
Lin, R.Y. et al. (2010). "Measured Immunoglobulin E in Allergic Bronchopulmonary Aspergillosis Treated with Omalizumab," J. Asthma 47:942-945.
Long, A.J. et al. (2021), "Efficacy of Eight-Week Omalizumab Monotherapy in Desensitization of Multi-Food Allergic Patients," Allergy 76(Suppl. 110):45, Abstract 776, 1-page.
Lowe, P.J. et al. (2015, e-pub. Dec. 8, 2014). "Revision of Omalizumab Dosing Table for Dosing Every 4 instead of 2 Weeks for Specific Ranges of Bodyweight and Baseline IgE," Regulatory Toxicology and Pharmacology 71:68-77.
Lowe, P.J. et al. (2016). "Integrated Quantitation of Biotherapeutic Drug-Target Binding, Biomarkers, and Clinical Response to Sup-

(56) References Cited

OTHER PUBLICATIONS port Rational Dose Regimen Selection," Chapter 13 in ADME and Translational Pharmacokinetics/Pharmacodynamics of Therapeutic Proteins: Applications in Drug Discovery and Development, H. Zhou and F-P Theil (eds). John Wiley & Sons, Inc., pp. 175-195.
Macginnitie, A.J. et al. (2017). "Omalizumab Facilitates Rapid Oral Desensitization for Peanut Allergy," J. Allergy Clin. Immunol. 139(3):873-881.e8, plus supplemental materials, 34 pages.
Macglashan, D.W. et al. (2012, e-pub. Jul. 15, 2012). "Suppression of the Basophil Response to Allergen During Treatment with Omalizumab is Dependent on 2 Competing Factors," J. Allergy Clin. Immunol. 130(5):1130-1135, plus supplemental figures, 11 pages.
Manohar, M. et al. (2014). "The Potential of Anti-IgE in Food Allergy Therapy," Curr. Treat. Options Allergy 1(2):145-156, 13 pages.
Manohar, M. et al. (2021). "Immune Changes Beyond Th2 Pathways During Rapid Multifood Immunotherapy Enabled with Omalizumab," Allergy 76(9):2809-2826, 27 pages.
Mari, A. et al. (2017). "Omalizumab Treatment for Severe Food Allergy Caused by Lipid Transfer Protein: A Preliminary Case Series," Allergy, 72(Suppl. 103):338, Abstract No. 0501, 1 page.
Martinez, F.D. (2019). "Childhood Asthma Inception and Progression: Role of Microbial Exposures, Susceptibility to Viruses and Early Allergic Sensitization," Immunol. Allergy Clin. North Am. 39(2):141-150, 11 pages.
Martorell-Calatayud, C. et al. (2016). "Anti-IgE-Assisted Desensitization to Egg and Cow's Milk in Patients Refractory to Conventional Oral Immunotherapy," Pediatr. Allergy Immunol., 27(5):544-546.
Mcgowan, E.C. et al. (2013). "Prevalence of Self-Reported Food Allergy in the National Health and Nutrition Examination Survey (NHANES) 2007-2010," J. Allergy Clin. Immunol. 132(5):1-6, 6 pages.
Mcgowan, E.C. et al. (2014). "Relationship of IgE to Basophil Phenotypes in Peanut-Sensitized Adults," J. Allergy Clin. Immunol 134(3):746-749, 7 pages.
Mendonca, V. et al. (2011). "Omalizumab in Pediatric Patients with Severe Food Allergy," Allergy 66(Suppl. 94):1-104, Abstract 135, 2 pages.
Mendonça, R.B. et al. (2012, e-pub. Jul. 12, 2011). "Open Oral Food Challenge in the Confirmation of Cow's Milk Allergy Mediated by Immunoglobulin E," Allergologia et Immunopathologia 40(1):25-30.
Mennini, M. et al. (2018). "Omalizumab with Severe Food Allergy: Perhaps More Than a Simple Good Idea," J. Ped. Gastroenterology and Nutrition 66(Suppl. 2):315, 1 page.
Mutarelli, A. et al. (2023). Biological in IgE-Mediated Food Allergy, Curr. Opin. Allergy Clin. Immunol. 23:205-209.
Nadeau, K.C. et al. (2011). "Rapid Oral Desensitization in Combination with Omalizumab Therapy in Patients with Cow's Milk Allergy," J. Allergy Clin. Immunol. 127(6):1622-1624, 5 pages.
Nilsson, C. et al. (2014). "Successful Management of Severe Cow's Milk Allergy with Omalizumab Treatment and CD-sens Monitoring," Asia Pacifica Allergy 4:257-260.
Nishie, M. et al. (2021, e-pub. Jul. 9, 2021). "Successful Treatment of a Patient with Adult Food Allergy and Severe Asthma Using Omalizumab," Asia Pacific Allergy 11(3):e27, 5 pages.
Noone, S. et al. (2015, e-pub. Jan. 13, 2015). "Epinephrine Use in Positive Oral Food Challenges Performed as a Screening Test for Food Allergy Therapy Trials," J. Allergy Clin. Immunol. Pract. 3(3):424-428, 11 pages.
Park, S.Y. et al. (2010). "Recalcitrant Atopic Dermatitis Treated with Omalizumab." Ann. Dermatol. 22(3):349-352.
Peloche, M.P. et al. (2011). "Severe Food Allergy in Children. Omalizumab as an Alternative Treatment to Elimination Diet," Clinical and Translational Allergy 1(Suppl. 1):p. 55, 1 page.
Phipatanakul, W. et al. (2021, e-pub. Nov. 24, 2020). "Preventing Asthma in High Risk Kids (PARK) with Omalizumab: Design, Rationale, Methods, Lessons Learned and Adaptation," Contemporary Clinical Trials and Supplemental Information 100:106228, 18 pages.
Prussin, C. et al. (2003). "Omalizumab Treatment Downregulates Dendritic Cell FcεRI Expression," J. Allergy Clin. Immunol. 112(6):1147-1154.
Rafi, A. et al. (2010). "Effects of Omalizumab in Patients with Food Allergy," Allergy Asthma Proc. 31(1):76-83.
Ramírez, Del Pozo, M.E. et al. (2011). "Omalizumab (An Anati-IgE Antibody) in the Treatment of Severe Atopic Eczema," J. Investig. Allergol. Clin. Immunol 21:410-421.
Randhawa, I. et al. (2009, e-pub. Jul. 21, 2009). "Resolution of Corticosteroid-Induced Diabetes in Allergic Bronchopulmonary Asspergillosis with Omalizumab Therapy: A Novel Approach," J. Asthma 46:445-447.
Rocha, R. et al. (2011, e-pub. Aug. 2, 2011). "Omalizumab in the Treatment of Eosinophilic Esophagitis and Food Allergy," Eur. J. Pediatr. 170:1471-1474.
Sabroe, R.A. et al. (2009). "Failure of Omalizumab in Cholinergic Urticaria," Clin. Exp. Dermatol. 35:e127-e129.
Salari, F. et al. (2022). "The Effectiveness of Oral Immunotherapy in Patients with Sesame Anaphylaxis Using Omalizumab," Clinical Medicine & Research 20(3):125-132.
Sampson, H. A. et al. (2011). "A Phase II, Randomized, Double Blind, Parallel Group, Placebo Controlled Oral Food Challenge Trial of Xolair (omalizumab) in Peanut Allergy," J. Allergy Clin. Immunol. 127(5):1309-1310, 3 pages.
Sampson, H.A. et al. (2019). "The Consortium for Food Allergy Research (CoFAR): The First Generation," J. Allergy Clin. Immunol. 143(2):486-493, 18 pages.
Sastre, I. et al. (2012). "A Case of Allergic Bronchopulmonary Aspergillosis Treated with Omalizumab," J. Investig. Allergol. Clin. Immunol. 22(2):133-153.
Savage, J. et al. (2016). "The Natural History of Food Allergy," J. Allergy Clin. Immunol. Pract. 4(2):196-203.
Savage, J.H. et al. (2012). "Kinetics of Mast Cell, Basophil, and Oral Food Challenge Responses in Omalizumab-Treated Adults with Peanut Allergy," J. Allergy Clin. Immunol 130:1123-1129.
Schneider, L.C. et al. (2013). "A Pilot Study of Omalizumab to Facilitate Rapid Oral Desensitization in High-Risk Peanut Allergic Patients," J. Allergy Clin. Immunol 132(6):1368-1374, 16 pages.
Sheinkopf, L.E. et al. (2008). "Efficacy of Omalizumab in the Treatment of Atopic Dermatitis: A Pilot Study," Allergy Asthma Proc. 29(5):530-537.
Sicherer, S.H. et al. (2014, e-pub. Dec. 31, 2013). "Food Allergy: Epidemiology, Pathogenesis, Diagnosis, and Treatment," J. Allergy Clin. Immunol. 133:291-307, 22 pages.
Sindher, S.B. et al. (2022). "Phase 2, Randomized Multi Oral Immunotherapy with Omalizumab 'Real Life' Study," European Academy of Allergy and Clinical Immunology 77:1873-1884.
Sorkness, C.A. et al. (2013). "Reassessment of Omalizumab-Dosing Strategies and Pharmacodynamics in Inner-City Children and Adolescents," J. Allergy Clin. Immunol: In Practice, pp. 163-171.
Spector, S.L. et al. (2007). "Effect of Omalizumab on Patients with Chronic Urticaria," Ann. Allergy Asthma Immunol. 99:190-193.
Takahashi, M. et al. (2017, e-pub. Dec. 12, 2017). "Oral Immunotherapy Combined with Omalizumab for High-Risk Cow's Milk Allergy: A Randomized Controlled Trial," Scientific Reports 7:17453, 10 pages.
Thaiwat, S. et al. (2011). "Omalizumab Treatment in Severe Adult Atopic Dermatitis," Asian Pac. J. Allergy Immunol. 29:357-360.
Toledo, F. et al. (2011). "Combined Therapy with Low-Dose Omalizumab and Intravenous Immunoglobulin for Severe Atopic Dermatitis. Report of Four Cases," J. Eur. Acad. Dermatiol. Venereol 26:1325-1327.
Van Der Ent, C.K. et al. (2007). "Successful Treatment of Allergic Bronchopulmonary Aspergillosis with Recombinant Anti-IgE Antibody," Thorax 62:276-277.
Velling, P. et al. (2011). "Improvement of Quality of Life in Patients with Concomitant Allergic Asthma and Atopic Dermatitis: One Year Follow-Up of Omalizumab Therapy," Eur. J. Med. Res. 15:407-410.
Vickery, B.P. et al. (2019). "Can Omalizumab Monotherapy Benefit Real-World Food Allergy Patients? Lessons From an Observational Study," J. Allergy Clin. Immunol. Pract. 7(6):1910-1911.

(56) References Cited

OTHER PUBLICATIONS

Vigo, P.G. et al. (2006). "Efficacy of Anti-IgE Therapy in Patients with Atopic Dermatitis," J. Am. Acad. Dermatiol. 55:168-170.
Wang, Z. et al. (2021). "Traditional Chinese Medicine for Food Allergy and Eczema," Ann. Allergy Asthma Immunol. 126(6):639-654.
Warrier, P. et al. (2009). "Omalizumab in Idiopathic Anaphylaxis," Ann. Allergy Asthma Immunol. 102:257-258.
Wood, R.A. (2017). "Oral Immunotherapy for Food Allergy," J. Investig. Allergol. Clin. Immunol. 27(3):151-159.
Wood, R.A. (2016). "Food Allergen Immunotherapy: Current Status and Prospects for the Future," J. Allergy Clin. Immunol. 137:973-982.
Wood, R.A. et al. (2016). "A Randomized Double-Blind Placebo-Controlled Study of Omalizumab Combined with Oral Immunotherapy for the Treatment of Cow's Milk Allergy," J. Allergy Clin. Immunol. 137(4):1103-1110.e1-11, 22 pages.
Wood, R.A. et al. (2024, e-pub. Feb. 25, 2024). "Omalizumab for the Treatment of Multiple Food Allergies," The New England Journal of Medicine 390(10):889-899.
Wood, R.A. et al. (2022, e-pub. Jul. 21, 2022). "Protocol Design and Synopsis: Omalizumab as Monotherapy and as Adjunct Therapy to Multiallergen OIT in Children and Adults with Food Allergy (OUtMATCH)," J. Allergy Clin. Immunol. Global and Supplemental Information, 17 pages.
Xolair® (2015). "Summary of Product Characteristics," European Public Assessment Report. 259 pages.
Xolair® (Jul. 21, 2015). "Australian Product Information for Omalizumab," Australian Public Assessment Report. 33 pages.
Xolair® (Mar. 22, 2023). "Summary of Product Characteristics," European Public Assessment Report. 179 pages.
Xolair® (Nov. 25, 2005). "Scientific Discussion," European Public Assessment Report. 34 pages.
Zirbes, J.M. et al. (2008). "Steroid-Sparing Effect of Omalizumab for Allergic Bronchopulmonary Aspergillosis and Cystic Fibrosis," Pediatri. Pulmonol. 43:607-610.
Zuberbier, T. et al. (2023, e-pub. Dec. 15, 2022). "Omalizumab in IgE-Mediated Food Allergy: A Systematic Review and Meta-Analysis," J. Allergy Clin. Immunol. Part. 11:1134-1146.
Chinuki, Y. et al. (2020, e-pub. Nov. 18, 2019). "In Vitro Basophil Activation is Reduced by Short-Term Omalizumab Treatment in Hydrolyzed Wheat Protein Allergy," Allergology International 69:284-286.
2 to 20 years: Boys Stature-for-Age and Weight for Age Percentiles, Centers for Disease Control and Prevention, (Nov. 21, 2000), available at <https://www.cdc.gov/growthcharts/data/set1clinical/cj41c021.pdf>, 1 page.
2 to 20 years: Girls Stature-For-Age and Weight for Age Percentiles, Centers for Disease Control and Prevention, (Nov. 21, 2000), available at <https://www.cdc.gov/growthcharts/data/set1clinical/cj41c022.pdf>, 1 page.
Amneal Pharmaceuticals, Inc. and Kashiv Biosciences, "Petition for Inter Partes Review of U.S. Pat. No. 12,030,959," IPR2026-00260, May 26, 2026, 79 pages.
Anonymous (Aug. 1, 2019). "Clinical Trial to Evaluate Experimental Treatment in People Allergic to Multiple Foods," National Institutes of Health, 4 pages.
Arasi, S. et al. (Feb. 2019). "Omalizumab Gets Tolerance in Patients With Severe Food Allergy: A Real-Live Study," J. Allergy Clin. Immunol. 143(2):Abstracts AB271, Abstract # 822, 2 pages.
Birth to 24 months: Boys Length-For-Age and Weight-for-Age Percentiles, Centers for Disease Control and Prevention (Nov. 1, 2009), available at <https://www.cdc.gov/growthcharts/data/who/GrChrt_Boys_24LW_100611.pdf>, 1 page.
Birth to 24 months: Girls Length-For-Age and Weight-for-Age Percentiles, Centers for Disease Control and Prevention (Nov. 1, 2009), available at <https://www.cdc.gov/growthcharts/data/who/GrChrt_Girls_24LW_9210.pdf>, 1 page.
Breakthrough Therapy (Jan. 4, 2018). Food and Drug Administration, available at <https://www.fda.gov/patients/fast-track-breakthrough-therapy-accelerated-approval-priority-review/breakthrough-therapy>, last visited Oct. 2, 2025, 2 pages.
Clinical Trials NCT03881696 (Records History, Version 26, May 2, 2022, Last Update Posted Sep. 10, 2025). "Omalizumab as Monotherapy and as Adjunct Therapy to Multi-Allergen OIT in Food Allergic Participants (OUtMatch)," retrieved from the Internet, <https://clinicaltrials.gov/study/NCT03881696?tab=history&a=26#version-content-panel>, 40 pages.
Consortium for Food Allergy Research (Jun. 7, 2024). "Protocol CoFAR-11 Omalizumab as Monotherapy and as Adjunct Therapy to Multi-Allergen OIT in Food Allergic Children and Adults OUtMATCH", Version 10.0 dated Jun. 7, 2024, 157 pages.
Crisafulli, G. et al. (Jan. 14, 2019). "Omalizumab in Children with Severe Allergic Disease: A Case Series," Italian J. Pediatrics 451:13, 11 pages.
Declaration of Dr. Asif Rafi, dated May 22, 2026, in Support of Petition for Inter Partes Reviewed of U.S. Pat. No. 12,030,959, 150 pages plus Curriculum Vitae of Dr. Asif Rafi, 9 pages.
Gupta, R.A. et al. (2018). "The Public Health Impact of Parent-Reported Childhood Food Allergies in the United States," Pediatrics 142(6):e20181235, 12 pages.
Humbert, M. et al. (2019). "IgE-Mediated Multimorbidities in Allergic Asthma and the Potential for Omalizumab Therapy," J. Allergy Clin. Immunol. Pract. 7:1418-1429.
International Preliminary Report on Patentability, issued on Dec. 23, 2025, for PCT Application No. PCT/US2023/070637, filed on Jul. 20, 2023, 7 pages.
International Preliminary Report on Patentability, issued on Dec. 23, 2025, for PCT Application No. PCT/US2023/070639, filed on Jul. 20, 2023, 8 pages.
Manti, S. et al. (Jul. 5, 2021). "Monoclonal Antibodies in Treating Food Allergy: A New Therapeutic Horizon," Nutrients 13:2314, 13 pages.
Mennini, M. et al. (Nov. 16, 2017). "Omalizumab Gets Tolerance in Patients With Severe Food Allergy," in Meeting Abstracts, Proceedings of the 2017—World Allergy Org. J. 10(Suppl. 2):39, p. 15, Abstract A42, 16 pages.
Mori, F. et al. (Sep. 28, 2021). "Oral Immunotherapy for Food-Allergic Children: A Pro-Con Debate," Frontiers in Immunol. 12:636612, 15 pages.
National Institutes of Health (Feb. 29, 2000). "Press Release: National Institutes of Health Launches 'ClinicalTrials.gov'," U.S. National Library of Medicine, retrieved from the Internet <https://www.nlm.nih.gov/archive/20040831/news/ press_releases/clntrlpr00.html>, 6 pages.
Navinés-Ferrer, A. et al. (2016). "IgE-Related Chronic Diseases and Anti-IgE-Based Treatments," J. Immunol. Res. 2016:8163803, 12 pages.
Nishima, S. et al. (Jan. 2019). Omalizumab and Unmet Needs in Severe Asthma and Allergic Comorbidities in Japanese Children: Asia Pacific Allergy 9(1):e7, 13 pages.
Peloche, M.P. et al. (Feb. 2011). "Treatment of Severe and Persistent Food Allergy With Omalizumab," J. Allergy Clin. Immunol. Abstract # 88, 2 pages.
Saab, I. et al. (Mar./Apr. 2022). "Trends in Food Allergy Research, Regulations and Patient Care," Nutrition Today 57(2):64-68.
Sandström, T. (May 5, 2009). "Omalizumab in the Management of Patients with Allergic (IgE-Mediated) Asthma," J. Asthma & Allergy 2:49-62.
Xolair® (2003). "Omalizumab," Food and Drug Administration ("PI2003"), 17 pages.
Xolair® (Jul. 2016). "Prescribing Information," Food and Drug Administration ("PI2016"), 27 pages.
Xolair® (Jul. 2021). "Prescribing Information," Food and Drug Administration, ("PI2021"), 52 pages.
Xolair® (Sep. 2014). "Prescribing Information," Food and Drug Administration ("PI2014"), 26 pages.
Xolair® (Feb. 2024). "Prescribing Information," Food and Drug Administration, with patient package insert, 86 pages.
Zhu, R. et al. (2021). "Pharmacokinetics and Exposure-Efficacy Relationships of Omalizumab in Patients with Nasal Polyps," Pulmonary Pharmacology & Therapeutics 71:102080, 12 pages.

(56) References Cited

OTHER PUBLICATIONS

Bégin, P. et al. (2014). "Phase 1 Results of Safety and Tolerability in a Rush Oral Immunotherapy Protocol to Multiple Foods Using Omalizumab," Allergy, Asthma & Clinical Immunology 10:7, plus supplemental materials 13 pages.

* cited by examiner

| | Body Weight (kg) | | | | | | | | | | | | |
|---|---|---|---|---|---|---|---|---|---|---|---|---|---|
| Baseline IgE (IU/mL) | ≥10-12 | >12-15 | >15-20 | >20-25 | >25-30 | >30-40 | >40-50 | >50-60 | >60-70 | >70-80 | >80-90 | >90-125 | >125-150 |
| ≥30-100 | 75 | 75 | 75 | 75 | 75 | 75 | 150 | 150 | 150 | 150 | 150 | 300 | 300 |
| >100-200 | 75 | 75 | 75 | 150 | 150 | 150 | 300 | 300 | 300 | 300 | 300 | 450 | 600 |
| >200-300 | 75 | 75 | 150 | 150 | 150 | 225 | 300 | 300 | 450 | 450 | 450 | 600 | 375 |
| >300-400 | 150 | 150 | 150 | 225 | 225 | 300 | 450 | 450 | 450 | 600 | 600 | 450 | 525 |
| >400-500 | 150 | 150 | 225 | 225 | 300 | 450 | 450 | 600 | 600 | 375 | 375 | 525 | 600 |
| >500-600 | 150 | 150 | 225 | 300 | 300 | 450 | 600 | 600 | 375 | 450 | 450 | 600 | |
| >600-700 | 150 | 150 | 225 | 300 | 225 | 450 | 600 | 375 | 450 | 450 | 525 | | |
| >700-800 | 150 | 150 | 150 | 225 | 225 | 300 | 375 | 450 | 450 | 525 | 600 | | |
| >800-900 | 150 | 150 | 150 | 225 | 225 | 300 | 375 | 450 | 525 | 600 | | | |
| >900-1000 | 150 | 150 | 225 | 225 | 300 | 375 | 450 | 525 | 600 | | | | |
| >1000-1100 | 150 | 150 | 225 | 225 | 300 | 375 | 450 | 600 | | | | | |
| >1100-1200 | 150 | 150 | 225 | 300 | 300 | 450 | 525 | 600 | | | | DO NOT DOSE | |
| >1200-1300 | 150 | 225 | 225 | 300 | 375 | 450 | 525 | | | | | | |
| >1300-1500 | 150 | 225 | 300 | 300 | 375 | 525 | 600 | | | | | | |
| >1500-1850 | | 225 | 300 | 375 | 450 | 600 | | | | | | | |

Dosing frequency:

- Dose every 4 weeks
- Dose every 2 weeks
- Do not dose

FIG. 2

ANTI-IgE ANTIBODY THERAPY FOR MULTIPLE FOOD ALLERGIES

CROSS-REFERENCE TO RELATED APPLICATIONS

This application is a continuation of U.S. application Ser. No. 19/050,002, filed Feb. 10, 2025, which is a continuation of U.S. application Ser. No. 18/735,125, filed Jun. 5, 2024, now abandoned, which is a continuation of U.S. application Ser. No. 18/486,053, filed Oct. 12, 2023, now U.S. Pat. No. 12,030,959, which is a continuation of International Application No. PCT/US2023/070639, filed internationally on Jul. 20, 2023, which claims the benefit of U.S. Provisional Application No. 63/512,051, filed Jul. 5, 2023, the content of each of which is hereby incorporated by reference in its entirety.

STATEMENT REGARDING FEDERALLY SPONSORED RESEARCH OR DEVELOPMENT

This invention was made with government support under cooperative agreements, AI130836 and AI130838, awarded by the National Institutes of Health (NIH). The government has certain rights in the invention.

REFERENCE TO AN ELECTRONIC SEQUENCE LISTING

The content of the electronic sequence listing (146392066804seqlist.xml; Size: 10,952 bytes; and Date of Creation: Sep. 15, 2025) is herein incorporated by reference in its entirety.

FIELD OF THE INVENTION

The present disclosure provides methods and kits for treating or preventing an allergic reaction to a food allergen consumed by a human subject with one or more food allergies. In particular, the present disclosure provides prophylactic therapies comprising administration of an anti-IgE antibody at a specific dose to a human subject who is allergic to one or more food allergens.

BACKGROUND OF THE INVENTION

Food allergy affects approximately 15 million patients in the U.S., including six million children. It causes substantial morbidity and mortality, and it is the most common cause of anaphylaxis in pediatric patients seen in emergency departments across the U.S. (Gupta et al., JAMA Pediatr, 167: 1026-1031, 2013). Significant consequences, including death, can result from exposure to food allergens by patients who are allergic to those food allergens, and the standard of care is merely avoidance of those food allergens. Often, life-saving treatment with antihistamines and epinephrine autoinjectors is necessary for acute allergic reactions to food allergens.

While an oral immunotherapy for peanut allergy has been approved by the United States Food and Drug Administration (USFDA), substantial gaps remain. Most important among these gaps include treatment for foods other than peanut and treatment of patients who are allergic to multiple foods. This is an unmet need, as 40% to 70% of children and adults with peanut allergy are indeed allergic to other foods (Sicherer et al., J Allergy Clin Immunol, 133:291-307, 2014; and Brough et al., J Allergy Clin Immunol, 145:1231-1239, 2020). There is, therefore, a substantial need for improved therapies for reducing or preventing allergic reactions to food allergens in patients allergic to those food allergens.

SUMMARY OF THE INVENTION

The present disclosure provides methods and kits for treating a subject having or diagnosed with a food allergy to one or more food allergens. In particular, the present disclosure provides prophylactic therapies comprising administration of an anti-IgE antibody at a specific dose and frequency to a human subject who is allergic to one or more food allergens.

BRIEF DESCRIPTION OF DRAWINGS

FIG. 2 is a dosing table for omalizumab based on body weight and baseline total serum IgE of the patient. The dosing frequency is indicated by each cell: gray shading is once every 4 weeks; no shading is once every 2 weeks; and black shading is do not dose.

DETAILED DESCRIPTION OF THE INVENTION

Figure 1:
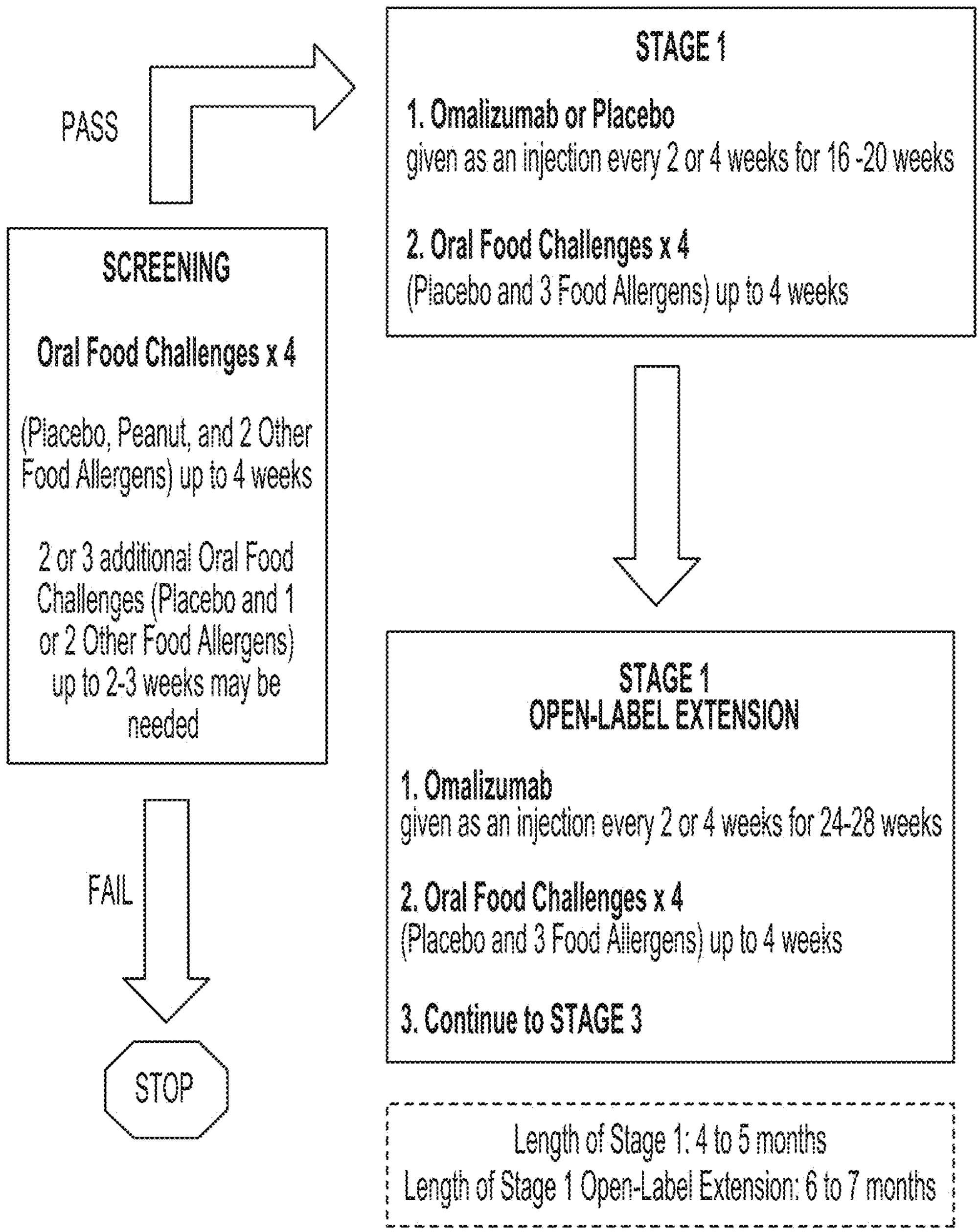
FIG. 1 is a flow chart of a study design for testing omalizumab in food allergy, including Screening, Stage 1, and Stage 1 open label extension phases of the study as described in Example 1 herein.

The present disclosure provides methods and kits for treating a human subject having or diagnosed with a food allergy to one or more food allergens. In some embodiments, the subject is practicing food avoidance. In other embodiments, the subject has or may accidentally consume a food containing the one or more food allergens. In some embodiments, the subject is at risk of being exposed to the one or more food allergens. In some embodiments, the treating prevents or reduces an allergic reaction in the subject following consumption of food containing the one or more food allergens. In particular, the present disclosure provides prophylactic therapies comprising administration of an anti-IgE antibody at a specific dose and frequency to a human subject. In some embodiments, the human subject is allergic to one or more food allergens. In some embodiments, the human subject is allergic to peanuts and one, two or more additional food allergens. In some embodiments, the subject is a child. In some embodiments, the child is less than 6 years of age. In some embodiments, the child is from 1 to 5 years of age. In a preferred embodiment, the anti-IgE antibody is omalizumab.

As described in Example 1, a Phase 3 clinical study (OUtMATCH) is being conducted to study the use of omalizumab for the treatment of patients with a food allergy. In Stage 1 of the study, omalizumab monotherapy was found to be surprisingly safe and effective. Specifically, this outcome was particularly striking in young children (1-5 years of age), for whom XOLAIR® (omalizumab marketed by Genentech USA, Inc., South San Francisco, CA, and Novartis Pharmaceuticals Corporation, East Hanover, NJ) has not been previously approved by the USFDA for other indications (persistent allergic asthma, nasal polyps, and chronic spontaneous urticaria). This finding is a major advance in the treatment of children with multiple food allergies and is an effective therapy without the need for a food-specific treatment such as oral immunotherapy (OIT).

Successful completion of this study depended in part on design of a new dosing table which accommodates patients having a body weight ranging from 10-20 kg and having baseline total serum IgE levels as high as 1850 IU/mL. Omalizumab doses for these weights and serum IgE levels had not been previously determined because there have been no prior regulatory approvals of omalizumab for patients under 6 years of age. Moreover, patients suffering from food allergies on average have higher baseline total serum IgE levels. For example, the average baseline total serum IgE levels for subjects enrolled in a phase 3 study for use of omalizumab to treat asthma was 172.5 IU/ml (Busse et al., J Allergy Clin Immunol, 108:184-190, 2001), while the average baseline total serum IgE levels for subjects enrolled in two phase 3 studies for use of omalizumab to treat nasal polyps was 168 IU/mL and 218 UI/mL, respectively (Xolair® Prescribing Information). The subjects enrolled in this OUtMATCH study had an average baseline total serum IgE level of 810 IU/mL. Accordingly, it was important to determine doses which were high enough to produce a therapeutic benefit by reducing levels of serum IgE from relatively high baseline levels while also ensuring an acceptable safety profile.

Definitions

As used herein and in the appended claims, the singular forms "a," "an," and "the" include plural references unless indicated otherwise. For example, "a food allergy" includes one or more food allergies.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

The term "about" as used herein in reference to a value, encompasses from 95% to 105% of that value. For instance, a dose of about 150 g/L omalizumab refers to a dose of from 142.5 g/L omalizumab to 157.5 g/L omalizumab and includes 150 g/L omalizumab.

A "food allergen" is a food, typically a food containing protein(s), that can trigger an allergic reaction upon consumption of the food or at times just exposure to minute amounts of the food by a sensitive individual. Common food allergens of human subjects are peanut, milk, egg, cereal (e.g., wheat, barley, oats, etc.), tree nuts (cashew, hazelnut, walnut, etc.), sesame, soy, crustaceans (e.g., crab, oyster, shrimp, etc.) and fish (e.g., bass, flounder, cod, etc.).

The term "total serum IgE" or "serum total IgE" refers to a total amount of IgE present in a serum sample. Serum total IgE can be measured, for example, by an ELISA (enzyme-linked immunosorbent assay). One example of an ELISA to measure serum total IgE is the ImmunoCAP® assay (ThermoFisher Scientific). "Total IgE" includes free, unbound IgE and IgE complexed with a binding partner. "Free IgE" refers to IgE not bound to a binding partner.

The term "allergen-specific IgE" as used herein refers to IgE that is specific to a particular antigen, resulting from an initial exposure to allergen in a process known as allergy sensitization. In this process, the IgE binds the surface of mast cells and basophils resulting in the activation of mast cells and basophils upon subsequent exposure to the same allergen.

As used herein, a "baseline" level, such as baseline level for body weight, serum total IgE, and allergen-specific IgE, in a human refers to the body weight of the subject or the level (concentration) of serum total IgE before the first dose of an anti-IgE antibody. These may be referred to herein as "pretreatment" values.

As used herein, the term "treatment" can include "prevention" or "reduction." As used herein, the term "prevention" includes providing prophylaxis with respect to occurrence or recurrence of an IgE-mediated disorder (e.g., allergic reaction to a food allergen) in an individual (e.g., human subject). As used herein, the term "reduction" includes lessening of the severity of symptoms as described in Table 1-1.

An "effective amount" or "therapeutically effective amount" of an agent or, e.g., a pharmaceutical formulation comprising the agent, refers to an amount effective, at dosages and for periods of time or at dosing frequency necessary, to achieve the desired therapeutic or prophylactic result, such as a measurable improvement in the state, e.g., reduction in symptoms such as those commonly experienced by a subject suffering from a food allergy. A therapeutically effective amount may reduce or prevent symptoms of a disorder.

As used herein, the terms, "prophylaxis," "prophylactic," "prophylactically," and the like refer to treatment to protect a subject from the occurrence or recurrence of an IgE-mediated disorder (e.g., allergic reaction to a food allergen) resulting from intentional or accidental exposure to or consumption of a food allergen.

The terms "determine" and "determining" as used herein refer to ascertaining a particular fact or piece of information about a patient, e.g., using an ELISA to determine the serum total IgE of a subject. Determining includes, e.g., querying a subject or referring to a document which contains the fact or piece of information about a subject, such as the body weight and/or serum total IgE of a patient.

The terms "allergic reaction" and "allergic response" as used herein refer to the experience by a human subject who is exposed to and/or consumes a food containing a food allergen to which the human subject is allergic, wherein the human subject experiences or exhibits dose-limiting symptoms which are mild, moderate, and/or severe symptoms which are characteristic of an allergic reaction to a food allergy.

The term "dose-limiting symptoms" or "food allergy reaction symptoms" as used herein refers to symptoms experienced by a subject having a food allergy wherein when the subject experiences a food allergic response or allergic reaction to one or more food allergens, the subject experiences one or more dose-limiting symptoms involving the skin, respiratory tract, and/or gastrointestinal tract, as well as neurological and/or circulatory symptoms.

The terms "mild," "moderate," and "severe" as used herein to characterize an allergic reaction in a subject which may be assessed by a trained expert (e.g., clinician or medical doctor) on food allergies and exposure to a food allergen. The grading scale used to define dose-limiting symptoms is shown below in Table 1-1.

TABLE 1-1

Dose-Limiting Symptoms

| Severity | Symptoms |
|---|---|
| Mild | Skin: limited or localized hives, swelling (e.g., mild lip edema), skin flushing (e.g., few areas of faint erythema) or mild pruritus (e.g., occasional scratching). |

TABLE 1-1-continued

| Dose-Limiting Symptoms | |
|---|---|
| Severity | Symptoms |
| | Respiratory: rhinorrhea (e.g., occasional sniffling or sneezing), nasal congestion, occasional cough, throat discomfort. |
| | GI: mild abdominal discomfort (including mild nausea with or without decreased activity), isolated emesis thought to be secondary to gag. |
| Moderate | Skin: systemic hives (e.g., numerous or widespread hives), swelling (e.g., significant lip or face edema), pruritus causing protracted scratching, more than a few areas of erythema or pronounced erythema. |
| | Respiratory: throat tightness without hoarseness, persistent cough, wheezing without dyspnea. |
| | GI: persistent moderate abdominal pain/cramping/nausea with decreased activity, vomiting. |
| Severe | Skin: severe generalized urticaria/angioedema/erythema. |
| | Respiratory: laryngeal edema, throat tightness with hoarseness, wheezing with dyspnea, stridor. |
| | GI: severe abdominal pain/cramping/repetitive vomiting. |
| | Neurological: change in mental status. |
| | Circulatory: clinically significant hypotension |

The term "oral immunotherapy" or "OIT" as used herein, refers to feeding a food allergen to an allergic individual in an increasing amount in order to desensitize the individual to the food. For instance, oral immunotherapy to peanut involves feeding peanut to an allergic individual at increasing amounts over a period of time to increase the threshold of peanut (amount in milligrams) that would trigger an allergic reaction upon consumption by the individual.

As used herein, the term "food avoidance" refers to the active effort or intent by a subject to not ingest or consume any foods that do or may contain a food allergen to which the subject knows or suspects he is allergic. A subject who practices food avoidance may accidentally be exposed to or unintentionally ingest or consume a food that contains the allergen(s) to which that subject is allergic.

I. Anti-IgE Antibodies

The methods, uses, medicaments and kits of the present disclosure for treating or preventing an allergic reaction to a food allergen consumed by a human subject with a food allergy to one or more food allergens involve administration of an anti-IgE antibody at a specific dose and frequency to the subject. In some embodiments, the subject is allergic to peanuts. In some embodiments, the subject is allergic to peanuts and one, two, or more additional food allergens. The anti-IgE antibodies of the methods and kits of the present disclosure block binding of human IgE to the high affinity human IgE Receptor ($Fc_{\varepsilon}RI$). In some embodiments, the anti-IgE antibody is omalizumab or monoclonal antibody comprising CDR-H1 (GYSITSGY, set forth as SEQ ID NO:5), CDR-H2 (TYDGS, set forth as SEQ ID NO:6), CDR-H3 (GSHYFGHWHFAV, set forth as SEQ ID NO:7), CDR-L1 (RASQSVDYDGDSYMN, set forth as SEQ ID NO:8), CDR-L2 (AASYLES, set forth as SEQ ID NO:9) and CDR-L3 (QQSHEDPYT, set forth as SEQ ID NO:10). In some preferred embodiments, the anti-IgE antibody is omalizumab. In other preferred embodiments, the anti-IgE antibody is a biosimilar of omalizumab.

Omalizumab (CAS Registry No. 242138-07-4) is a recombinant DNA-derived, humanized IgG1 monoclonal antibody with a molecular weight of approximately 149 kDa that selectively binds to human IgE. The amino acid sequences of the heavy chain variable region (VH) and the light chain variable region (VL) of omalizumab are shown as the E25 sequences in FIG. 2 of U.S. Pat. No. 6,172,213, and are set forth herein as SEQ ID NO:3 and SEQ ID NO: 4, respectively. The amino acid sequences of the full length heavy chain and the full length light chain of omalizumab are shown as the E25 sequences in FIG. 12 of U.S. Pat. No. 6,172,213, and are set forth herein as SEQ ID NO:1 and SEQ ID NO:2, respectively.

Omalizumab is designed to treat IgE-mediated disease by reducing the concentration of free IgE in blood and in tissue. Omalizumab selectively binds to human IgE at the same site of the IgE molecule that binds to the high affinity IgE Receptor ($Fc_{\varepsilon}RI$), thereby reducing IgE bound to the surface of basophils, mast cells, and dendritic cells and reducing basophil, mast cell, and dendritic cell-triggered Type 2 inflammation.

XOLAIR® (omalizumab marketed by Genentech USA, Inc., South San Francisco, CA, and Novartis Pharmaceuticals Corporation, East Hanover, NJ) is approved by the European Commission and the USFDA for treatment of other indications in older children and adults. Specifically, omalizumab is approved for patients with moderate-to-severe persistent asthma who are 6 years of age or older, and for patients with chronic idiopathic urticaria who are 12 years of age or older. However, omalizumab is not currently approved for treating food allergy in patients of any age.

Omalizumab is commercially available as a lyophilized powder contained in a single-use vial that is reconstituted with sterile water for injection. Omalizumab is administered by subcutaneous (SC) injection. It is also commercially available as a prefilled syringe administered by SC injection.

II. Treatment of a Human Subject Suffering From One or More Food Allergies

In the methods, uses, medicaments and kits of the present disclosure, an anti-IgE antibody, such as omalizumab, is administered to a human subject with a food allergy to one or more food allergens in an amount and/or dosing frequency to reduce or prevent an allergic reaction to consumption of the food containing the food allergen(s) by the human subject. The methods, uses, medicaments and kits of the present disclosure are contemplated to be especially valuable for pediatric patients (e.g., aged 1 year to less than 6 years) because accidental consumption is more difficult to avoid in this patient population. This is a vulnerable population where trials to assess adequacy of treatment benefit and defining safety parameters are more difficult to conduct. In some embodiments, omalizumab is to be used in conjunction with food allergen avoidance. In some embodiments, omalizumab is not indicated for the emergency treatment of allergic reactions. In some embodiments, omalizumab is not indicated for the emergency treatment of anaphylaxis.

A. Methods of Use

The present disclosure relates to methods of treating a human subject diagnosed with a food allergy to one or more food allergens with a therapeutically effective amount of omalizumab. In some embodiments, the methods of treating include preventing or reducing an allergic reaction to the one or more food allergens following exposure to or consumption by the subject. In some embodiments, the method of treating reduces the risk of an allergic reaction by the subject to exposure to or consumption of a food allergen to which the subject is allergic. In some embodiments, the method of treating reduces the severity of an allergic reaction to exposure to or consumption of a food allergen to which the subject is allergic. In some embodiments, the method of treating protects a human subject from an allergic reaction to a food allergen to which the subject is allergic.

In some embodiments, the method of treating comprises: administering to the subject a pharmaceutical composition comprising a therapeutically effective amount of omalizumab. In some embodiments, the pharmaceutical composition of omalizumab is administered to the subject by subcutaneous injection. In some embodiments, the therapeutically effective amount of omalizumab is administered to the subject prior to exposure to or consumption of the one or more food allergens. In some embodiments, the therapeutically effective amount of omalizumab is administered to the subject prophylactically prior to consumption of the one or more food allergens. In some embodiments, the method does not comprise concurrent oral immunotherapy with the food allergen. In some embodiments, the subject is practicing food avoidance.

In some embodiments, the subject is 1 year of age or older. In some embodiments, the subject is a child from about 1 year to about 5 years of age, from about 1 year to about 4 years of age, from about 1 year to about 3 years of age, from about 1 to about 2 years of age, or is about 1 year old. In some embodiments, the subject has not received an anti-IgE therapeutic prior to the treating. In some embodiments, the subject has not received an anti-IgE therapeutic less than 6 months, less than 1 year, less than 18 months, or less than 2 years prior to the disclosed treatment.

In some embodiments of the methods described herein, the methods further comprise determining the body weight and the total serum IgE level of the subject prior to administration of the first dose of omalizumab. It is understood that a subject may gain or lose body weight during the course of treating the subject with omalizumab for a food allergy. Accordingly, the dose amount and/or frequency may change during the course of treatment. In such a scenario, the dose of omalizumab may be changed relative to the first dose and in accordance with the dosing table of FIG. 2, wherein a subsequent dose (any dose which is administered after the first dose) is selected based on the body weight of the subject which is determined after the first dose but prior to the subsequent dose. The selection of the dose may not include consideration of a change in serum total IgE levels from the serum total IgE levels determined no more than 4 weeks, 2 weeks, 1 week, 5 days, 4 days, 3 days, 2 days, or 24 hours prior to the first dose (e.g., the baseline serum total IgE concentration). In some embodiments, the methods of treatment further comprise determining the body weight of the subject prior to administration of a subsequent dose of omalizumab to obtain a current body weight of the subject, wherein the subsequent dose administered to the subject is based on the current body weight of the subject at a time after the first dose and prior to the subsequent dose, and wherein the dose is based on the body weight of the subject prior to the subsequent dose and on the serum total IgE levels determined prior to the first dose of omalizumab and according to the dosing table shown in FIG. 2. In some embodiments, the subsequent dose is administered within 1 day, 1 week, 2 weeks, or 4 weeks of the determination of the current body weight of the subject. In some embodiments, the methods further comprise determining the age of the subject prior to administration of the first dose of omalizumab.

In some embodiments, the present disclosure further relates to methods of preventing an allergic reaction to consumption of a food allergen in a human subject with one or more food allergies, the method comprising: administering by subcutaneous injection once every two weeks to the subject a pharmaceutical composition comprising omalizumab, wherein prior to administration of a first dose of omalizumab to the subject, body weight of the subject is greater than 10 kg and less than or equal to 15 kg. In some embodiments, the method does not comprise concurrent oral immunotherapy with the food allergen.

The present disclosure also relates to methods of preventing an allergic reaction to consumption of a food allergen in a human subject with one or more food allergies, the method comprising: administering by subcutaneous injection once every two to four weeks to the subject a pharmaceutical composition comprising omalizumab, wherein prior to administration of a first dose of omalizumab to the subject, body weight of the subject is equal to or greater than 10 kg and less than or equal to 25 kg. In some embodiments, the method does not comprise concurrent oral immunotherapy with the food allergen.

In some embodiments, the food allergy comprises an allergy to peanut, milk, egg, wheat, cashew, hazelnut, or walnut, or a combination thereof, and the food allergen comprises peanut, milk, egg, wheat, cashew, hazelnut, or walnut, or a combination thereof. In some embodiments, the allergic reaction is a mild-to-moderate allergic reaction triggered by consumption of as little as about 100 mg to about 300 mg of the food allergen by the subject. In some embodiments, the allergic reaction is a moderate or moderate-to-severe allergic reaction triggered by consumption of as little as about 100 mg to about 300 mg of the food allergen by the subject. In some embodiments, the methods described herein permit the subject to consume a single dose of about 600 mg to about 1000 mg or more of the food allergen without triggering one or more dose-limiting symptoms or without triggering one or more moderate or severe dose-limiting symptoms. In some embodiments, the methods described herein permit the subject to consume a single dose of 100 mg, 200 mg, 300 mg, 400 mg, 500 mg, 600 mg, 700 mg, 800 mg, 900 mg, or 1000 mg of the food allergen without triggering one or more mild, moderate, and/or severe dose-limiting symptom. In some embodiments, the one or more dose-limiting symptoms comprise one or more:

skin: systemic hives, more than mild lip or face edema, pruritus causing protracted scratching, several areas of erythema pronounced erythema, and combinations thereof; and/or respiratory: throat tightness with or without hoarseness, persistent cough, wheezing with or without dyspnea, laryngeal edema, stridor, and combinations thereof; and/or gastrointestinal tract: moderate to severe abdominal pain, cramping, nausea, vomiting, and combinations thereof; and/or neurological: change in mental status; and/or circulatory: hypotension.

In some embodiments, without triggering dose-limiting symptoms in a subject treated with a dose of omalizumab comprises a lessening or lack of one or more dose-limiting symptoms. In some embodiments, without triggering dose-limiting symptoms in a subject treated with a dose of omalizumab comprises a lessening or lack of one or more moderate or severe dose-limiting symptoms.

In some embodiments of the methods described herein, the method of treatment with a therapeutically effective amount of omalizumab results in the reduction or prevention of an allergic response by a subject having a food allergy after that subject is exposed to or consumes food containing an allergen to which that subject is allergic. An allergic response can include but is not limited to several symptoms that are described in Table 1-1 as dose-limiting symptoms. These symptoms are categorized as mild, moderate, or severe. For example, a subject who has a food allergy will experience one or more symptoms described in Table 1-1 as a dose limiting response (mild, moderate, or severe) upon consumption of a food that contains the food allergen(s) to which the subject is allergic. In some embodiments, a subject who has a food allergy will experience one or more of the moderate or severe dose-limiting symptoms. Treatment according to the disclosure herein prevents an allergic reaction to a food allergen when after said treatment, the subject no longer experiences mild, moderate, and/or severe symptoms (Table 1-1). Treatment according to the disclosure herein reduces an allergic reaction to a food allergen when after said treatment, the subject experiences one or more symptoms as listed in Table 1-1 to a lesser extent level of severity than if they had not received treatment with omalizumab. In some embodiments, an expert in the field of food allergy would recognize a reduction or prevention of an allergic reaction by omalizumab treatment as described herein. In some embodiments, an ordinarily skilled artisan would recognize a reduction or prevention of an allergic reaction by omalizumab treatment as described herein. In embodiments, the methods described herein permit the subject to consume a single dose of about 600 mg to about 1000 mg or more of the food allergen without triggering an allergic reaction or dose-limiting symptom. In some embodiments, the methods described herein permit the subject to consume a single dose of about 600 mg to about 1000 mg or more of the food allergen while reducing the severity or frequency of an allergic reaction or dose-limiting symptom.

In some embodiments, the methods of treatment described herein reduce dose-limiting symptoms a subject experiences after the subject is exposed to or consumes a food allergen to which the subject is allergic. In some embodiments, the methods reduce one or more of the dose-limiting symptoms experienced by the subject from severe to moderate, from severe to mild, or from moderate to mild. In some embodiments, the methods of treatment described herein prevent dose-limiting symptoms a subject experiences after the subject is exposed to or consumes a food allergen to which that subject is allergic. In some embodiments, the methods prevent a subject who, prior to any treatment with omalizumab, experienced severe, moderate, and/or mild dose-limiting symptoms after exposure to or consumption of an allergen to which the subject is allergic, from experiencing any severe dose-limiting symptoms, from experiencing any moderate dose-limiting symptoms, and/or from experiencing any mild dose-limiting symptoms. In some embodiments, the mild dose-limiting symptoms include limited or localized hives, swelling of the skin (e.g., mild lip edema), skin flushing (e.g., few areas of faint erythema), mild pruritus (e.g., occasional scratching), rhinorrhea (e.g., occasional sniffling or sneezing), nasal congestion, occasional cough, throat discomfort, mild abdominal (gastrointestinal) discomfort including but not limited to mild nausea with or without decreased activity, and/or isolated emesis thought to be secondary to gag. In some embodiments, the moderate dose-limiting symptoms include systemic hives (e.g., numerous or widespread hives), swelling (e.g., significant lip or face edema), pruritus causing protracted scratching, more than a few areas of erythema or pronounced erythema. throat tightness without hoarseness, persistent cough, wheezing without dyspnea, persistent moderate abdominal pain/cramping/nausea with decreased activity, and/or vomiting. In some embodiments, the severe dose-limiting symptoms include severe generalized urticarial, angioedema, and/or erythema, laryngeal edema, throat tightness with hoarseness, wheezing with dyspnea, stridor, severe abdominal pain and/or cramping, repetitive vomiting, change in mental status, and/or clinically significant hypotension.

In some embodiments, the methods described herein reduce the allergic reaction in the subject when the subject is exposed to or consumes a food allergen to which the subject is allergic, wherein the subject, when administered a skin-prick test (SPT), experiences a wheal caused by the food allergen that is less than 4 mm, less than 3 mm, less than 2 mm, or less than 1 mm greater than a wheal caused by a saline control.

In some embodiments, the methods described herein decrease serum free IgE concentration in the subject by at least 95%, 96%, 97%, 98%, or 99% relative to serum free IgE concentration prior to the serum free IgE concentration in the subject prior to the first dose of omalizumab. In some embodiments, the decrease occurs after the first, second, third, fourth, fifth, sixth, seventh, eighth, ninth, or tenth dose of omalizumab. In some embodiments, free IgE is measured no more than 3 months, 2 months, 1 month, 2 weeks, or 1 week prior to a first dose of omalizumab. In some embodiments, free IgE in human serum is measured using a solid phase immunoenzymetric assay (IEMA).

Measurement of free IgE in the serum of a subject can be readily done, for example, according to the methods of Hamilton et al., J Immunol Methods, 303:81-91, 2005). In some embodiments, free IgE in human serum is measured using a solid phase enzyme IEMA in which IgE is captured from serum using anti-human IgE antibody and detected with labeled-FcεR1α.

In some embodiments, the methods described herein reduce the serum kilounits of allergen-specific IgE per liter ($kU_A/L$) in the serum of the patient. In some embodiments, the treatment reduces allergen-specific by at least 95%, 96%, 97%, 98%, or 99% relative to serum allergen-specific IgE concentration prior to the serum free IgE concentration in the subject prior to the first dose of omalizumab. In some embodiments, the decrease occurs after the first, second, third, fourth, fifth, sixth, seventh, eighth, ninth, or tenth dose of omalizumab. In some embodiments, to serum allergen-specific IgE is measured no more than 3 months, 2 months, 1 month, 2 weeks, or 1 week prior to a first dose of omalizumab. In some embodiments, to serum allergen-specific IgE in human serum is measured using an ELISA. In some embodiments, the allergen-specific IgE is peanut, milk, wheat, soy, egg, cashew, or hazelnut-specific IgE.

Measurement of allergen-specific IgE in serum can be readily done, for example, using the ThermoFisher ImmunoCAP™ specific IgE tests.

In some embodiments, the methods described herein reduce the likelihood the subject will require rescue treatment after consumption of the food allergen (e.g., a single dose of about 100 mg or more of peanut protein, and/or about 300 mg or more of milk, egg, wheat, cashew, hazelnut and/or walnut protein). In some embodiments, the rescue treatment comprises administration of an antihistamine or epinephrine. In some embodiments, the methods do not comprise concurrent oral immunotherapy to the food allergen. In other embodiments, the methods are useful in subjects who have failed prior oral immunotherapy.

In some embodiments, the disclosure provides an anti-IgE antibody for use as a medicament. In some embodiments, the anti-IgE antibody is omalizumab or a monoclonal antibody which comprises CDR-H1 (GYSITSGY, set forth as SEQ ID NO:5), CDR-H2 (TYDGS, set forth as SEQ ID NO:6), CDR-H3 (GSHYFGHWHFAV, set forth as SEQ ID NO: 7), CDR-L1 (RASQSVDYDGDSYMN, set forth as SEQ ID NO:8), CDR-L2 (AASYLES, set forth as SEQ ID NO:9) and CDR-L3 (QQSHEDPYT, set forth as SEQ ID NO:10). In some embodiments the use is in the treatment of a human subject diagnosed with or having a food allergy to one or more allergens according to the embodiments described herein. In some embodiments, the use further comprises administering to the subject a pharmaceutical composition comprising a therapeutically effective amount of the anti-IgE antibody such as omalizumab, e.g., as described herein. In some embodiments, the method does not comprise treating the subject with oral immunotherapy.

In some embodiments, the disclosure provides use of an anti-IgE antibody in the manufacture or preparation of a medicament. In some embodiments, the anti-IgE antibody is omalizumab or a monoclonal antibody which comprises CDR-H1 (GYSITSGY, set forth as SEQ ID NO: 5), CDR-H2 (TYDGS, set forth as SEQ ID NO:6), CDR-H3 (GSHYFGHWHFAV, set forth as SEQ ID NO:7), CDR-L1 (RASQSVDYDGDSYMN, set forth as SEQ ID NO:8), CDR-L2 (AASYLES, set forth as SEQ ID NO:9) and CDR-L3 (QQSHEDPYT, set forth as SEQ ID NO: 10). In some embodiments the medicament is for treatment of a food allergy to one or more allergens. In some embodiments, the medicament is for use in a method of treating the food allergy comprising administering to an individual having the food allergy to one or more allergens a therapeutically effective amount of the medicament such as a medicament comprising omalizumab. e.g., as described herein. In some embodiments, the method does not comprise treating the subject with oral immunotherapy.

i. Subjects

The treatment methods of the present disclosure are intended for use in human subjects. In some embodiments, the subject is 1 year of age or older. In some embodiments, the subject is a child (e.g., 1-10 years of age) or an adolescent (e.g., 11 to 18 years of age). In some embodiments, the subject is a child over 1 year of age and less than 6 years of age. In some embodiments, the child is from 1 year to 5 years of age. In some embodiments, the child is from about 1 year to about 4 years of age. In some embodiments, the child is from about 1 year to about 3 years of age. In some embodiments, the child is from about 1 year to about 2 years of age. In some embodiments, the child is about 1 year old.

In some embodiments, the subject has been identified as having a food allergy to any one or more food allergens. Food allergens may include at least one of the major food allergens identified by the United States Food and Drug Administration such as milk, eggs, fish (e.g., bass, flounder, cod), crustacean shellfish (e.g., crab, lobster, shrimp), tree nuts (e.g., almonds, walnuts, pecans), peanuts, wheat, soybeans and sesame. In some embodiments, the food allergen is selected from at least one of the group consisting of peanut, milk, egg, wheat, cashew, hazelnut, and/or walnut protein. In some embodiments, the food allergy comprises an allergy to at least one food allergen. In some embodiments, a food allergen is any food that causes and allergic reaction. In some embodiments, a food allergen refers to the protein in the food that causes the allergic response. In some embodiments, the one or more food allergens include but are not limited to peanut, milk, egg, wheat, cashew, hazelnut, and/or walnut protein. In some embodiments, the subject has a food allergy to peanut. In some embodiments, the subject has a food allergy to peanut, and one or more of milk, egg, wheat, cashew, hazelnut and walnut. In some embodiments, the subject has a food allergy to peanut, and two or more of milk, egg, wheat, cashew, hazelnut and walnut. In some embodiments, the subject has a food allergy to peanut, and three or more of milk, egg, wheat, cashew, hazelnut, and walnut.

In some embodiments, the subject has a food allergy to peanut, and four or more of milk, egg, wheat, cashew, hazelnut, and walnut. In some embodiments, the subject has a food allergy to peanut, and five or more of milk, egg, wheat, cashew, hazelnut, and walnut. In some embodiments, the subject has a food allergy to peanut, and milk, egg, wheat, cashew, hazelnut, and walnut. In some embodiments, the identification comprises a diagnosis of a food allergy by a physician.

In some embodiments, the allergic reaction is characterized as a mild allergic reaction or dose-limiting symptom. As used herein a "mild" allergic reaction includes manifestations in at least one of the skin, respiratory tract and gastrointestinal system (GI tract). Mild allergic reactions may manifest in the skin as limited or localized hives, swelling (e.g., mild lip edema), skin flushing (e.g., few areas of faint erythema) or mild pruritus (e.g., occasional scratching) and the like. Mild allergic reactions may manifest in the respiratory tract as rhinorrhea (e.g., occasional sniffling or sneezing), nasal congestion, occasional cough, throat discomfort and the like. Mild allergic reactions may manifest in the GI tract as mild abdominal discomfort (including mild nausea with or without decreased activity), isolated emesis thought to be secondary to gag and the like.

In some embodiments, the allergic reaction is characterized as a moderate allergic reaction or dose-limiting symptom. As used herein a "moderate" allergic reaction includes manifestations in at least one of the skin, respiratory tract and gastrointestinal system (GI tract). Moderate allergic reactions may manifest in the skin as systemic hives (e.g., numerous or widespread hives), swelling (e.g., significant lip or face edema), pruritus causing protracted scratching, more than a few areas of erythema or pronounced erythema and the like. Moderate allergic reactions may manifest in the respiratory tract as throat tightness without hoarseness, persistent cough, wheezing without dyspnea and the like. Moderate allergic reactions may manifest in the GI tract as persistent moderate abdominal pain/cramping/nausea with decreased activity, vomiting and the like.

In some embodiments, the allergic reaction is characterized as a severe allergic reaction or dose-limiting symptom. As used herein a "severe" allergic reaction includes manifestations in at least one of the skin, respiratory tract and gastrointestinal system (GI tract). Severe allergic reactions may manifest in the skin as severe generalized urticaria/angioedema/erythema and the like. Severe allergic reactions may manifest in the respiratory tract as laryngeal edema, throat tightness with hoarseness, wheezing with dyspnea, stridor and the like. Severe allergic reactions may manifest in the GI tract as severe abdominal pain/cramping/repetitive vomiting and the like. In addition, severe allergic reaction may include neurological and circulatory manifestations such as change in mental status and clinically significant hypotension, respectively.

In embodiments, mild-to-moderate allergic reaction may be triggered by consumption of as little as about 100 mg of the food allergen by the subject prior to treatment using the disclosed methods. In embodiments, mild-to-moderate allergic reaction may be triggered by consumption of as little as about 100 mg to about 300 mg of the food allergen by the subject prior to treatment using the disclosed methods.

In some embodiments, peanut allergy is diagnosed by the presence of a clinical history of food allergy. In some embodiments the peanut allergy is diagnosed or confirmed by one or more of: i. positive skin-prick test (SPT) (equal to or greater than 4 mm wheal greater than saline control) to peanut; ii. positive peanut IgE (equal to or greater than 6 kUA/L) determined by, e.g., an enzyme-linked immunosorbent assay (ELISA); and/or iii. positive blinded oral food challenge (OFC) to peanut defined as experiencing dose-limiting symptoms at a single dose of about 100 mg of peanut protein. In some embodiments, allergy to a food allergen (e.g., one or more of milk, egg, wheat, cashew, hazelnut and walnut) is diagnosed by one or more of: i. positive SPT (a wheal at least 4 mm greater than saline control) to the food allergen; ii. positive food allergen-specific IgE (equal to or greater than 6 kUA/L) determined by, e.g., an ELISA; and/or iii. positive blinded OFC to the food allergen defined as experiencing dose-limiting symptoms at a single dose of about 100 mg to about 300 mg of the food allergen protein. In some embodiments, the subject experiences dose-limiting symptoms to a single dose of about 100 mg of peanut protein, about 100 mg to about 300 mg protein for any two or more of milk, egg, wheat, cashew, hazelnut, and/or walnut protein, and no dose-limiting symptoms to placebo (e.g., oat) at any single dose up to about 100 to about 300 mg protein prior to administration of a pharmaceutical composition comprising an anti-IgE antibody (e.g., omalizumab).

In some embodiments, the subjects of the present disclosure do not have an IgE-mediated disorder that is not a food allergy (e.g., the only IgE-mediated disorder the subject is known to have is a food allergy). In some embodiments, the subjects of the present disclosure do not have asthma, nasal polyps, or chronic spontaneous urticaria at initiation of the treatment methods of the present disclosure. In some embodiments, the subjects of the present disclosure have not previously been diagnosed as having asthma, nasal polyps, or chronic spontaneous urticaria. In some embodiments, the subjects do not have asthma at initiation of the prophylactic methods of the present disclosure and have not previously been diagnosed as having asthma. In some embodiments, the subject has not been diagnosed with allergic rhinoconjunctivitis. In some embodiments, the subjects of the present disclosure have asthma, nasal polyps, or chronic spontaneous urticaria at initiation of the prophylactic methods of the present disclosure. In some embodiments, the subjects of the present disclosure have previously been diagnosed as having asthma, nasal polyps, or chronic spontaneous urticaria. In some embodiments, the subjects have asthma at initiation of the prophylactic methods of the present disclosure or have previously been diagnosed as having asthma. In some embodiments, the subject has been diagnosed with allergic rhinoconjunctivitis.

In some embodiments, the subjects of the present disclosure have not received anti-IgE therapy prior to initiation of the treatment methods of the present disclosure. In some embodiments, the subjects of the present disclosure have not received anti-IgE therapy less than 6 months, 1 year, 18 months, or 2 years prior to initiation of the treatment methods of the present disclosure.

ii. Dosing

The pharmaceutical composition is administered to the subject at a specific omalizumab dose and dosing interval based on the body weight and baseline total serum IgE concentration of the subject. The specific dose and dosing interval (frequency) is determined based on the dosing table described in FIG. 2 herein. Accordingly, prior to administration of the pharmaceutical composition, a body weight and a baseline total serum IgE level of the subject is determined. In some embodiments, when the body weight of the subject is equal to or greater than 10 kg and less than or equal to 25 kg and the baseline total serum IgE level is equal to or greater than 30 IU/ml and less than or equal to 2000 IU/ml, the omalizumab dose is from 75 mg to 375 mg and the dosing interval is every two to four weeks. In some embodiments, body weight is determined at baseline (prior to a first dose).

In some embodiments, body weight is determined at baseline (prior to administration of the first dose of the pharmaceutical composition). In some embodiments, total serum IgE level (concentration) is determined at baseline (prior to administration of the first dose of the pharmaceutical composition). In some embodiments, determining the baseline body weight and the baseline total serum IgE level of the subject is done no more than 3 months, 2 months, 1 month, 2 weeks, or 1 week prior to administration of a first dose of the pharmaceutical composition, preferably no more than 7, 6, 5, 4, 3, 2 or 1 day prior to administration of a first dose of the pharmaceutical composition.

In some embodiments, body weight of the subject is further determined prior to administration of a subsequent dose (post-baseline body weight) of the pharmaceutical composition. In some embodiments, the body weight is a post-baseline body weight of the subject, which is determined no more than two weeks prior to administration of each subsequent dose of the pharmaceutical composition, preferably no more than 7, 6, 5, 4, 3, 2 or 1 day prior to administration of each subsequent dose of the pharmaceutical composition. It is understood that a subject may gain or lose body weight during of the course of treating the subject with omalizumab for a food allergy. Accordingly, the dose amount and/or frequency may change during the course of treatment. In such a scenario, the dose of omalizumab may be changed relative to the first dose and in accordance with the dosing table of FIG. 2, wherein a subsequent dose (any dose after the first dose) is selected based on the body weight of the subject which is determined after the first dose but prior to the subsequent dose. The selection of the dose may not consider a change in serum total IgE levels from the baseline serum total IgE levels. Accordingly, in some embodiments, the methods of treatment further comprise determining the body weight of the subject prior to administration of a subsequent dose of omalizumab to obtain a current body weight of the subject, wherein the subsequent dose administered to the subject is based on the current body weight of the subject at a time after the first dose and prior to the subsequent dose, and wherein the dose is based on the body weight of the subject prior to the subsequent dose and on the serum total IgE levels determined prior to the first dose of omalizumab and according to the dosing table shown in FIG. 2. In some embodiments, the subsequent dose is administered within 1 day, 1 week, 2 weeks, or 4 weeks of the determination of the current body weight of the subject. In some embodiments, the methods further comprise determining the age of the subject prior to administration of the first dose of omalizumab.

In the methods and kits of the present disclosure, the body weight of the subject is from about 10 kg to about 25 kg. In the methods and kits of the present disclosure, the body weight of the subject is equal to or greater than 10 kg and less than or equal to 25 kg. In some embodiments, the body weight of the subject is equal to or greater than 10 kg and less than or equal to 20 kg. In some embodiments, the body weight of the subject is equal to or greater than 10 kg and less than or equal to 15 kg.

In some embodiments, total serum IgE is measured by an enzyme-linked immunosorbent assay (ELISA). In some embodiments, the baseline total serum IgE level is equal to or greater than 30 IU/ml and less than or equal to 2000 IU/ml. In some embodiments, the baseline total serum IgE level is from about 30 IU/ml to about 700 IU/ml. In some embodiments, the baseline total serum IgE level is from about 600 IU/ml to about 1850 IU/ml. In some embodiments, the baseline total serum IgE level is equal to or greater than 30 IU/ml and less than or equal to 1500 IU/ml. In some embodiments, the baseline total serum IgE level is from about 30 IU/ml to about 700 IU/ml. In some embodiments, the baseline total serum IgE level is from about 700 IU/ml to about 1500 IU/ml.

In certain embodiments, the dosing interval (also referred to herein as dosing frequency) is about once every 2 to 4 weeks and the duration of administration is at least 16 weeks to 12 months in length. In some embodiments, the dosing interval is every 2 weeks. In some embodiments, the dosing interval is every 4 weeks. In some embodiments, the duration of administration is at least about 16 to 20 weeks in length (e.g., from 4 to 10 total doses), at least about 16 to 40 weeks (e.g., from 4 to 20 total doses), or at least about 24 to 40 weeks (e.g., from about 6 to 20 total doses). In some embodiments, the duration of administration is at least about 10 to 12 months in length (e.g., from 10 to 24 total doses).

In some embodiments, the therapeutically effective amount of omalizumab is from about 150 mg to 300 mg, wherein prior to administration of a first dose of omalizumab to the subject, the body weight of the subject is equal to or greater than 10 kg and less than or equal to 20 kg, and the total serum IgE level of the subject is greater than 600 IU/ml. In some embodiments, the serum total IgE level of the subject is greater than 600 IU/ml and less than or equal to 1,850 IU/ml. In some embodiments, the dose of omalizumab is administered to the subject every about 2 weeks.

In some embodiments, the therapeutically effective amount of omalizumab is from about 375 mg to 450 mg, wherein prior to administration to the subject of a first dose of omalizumab, the body weight of the subject is greater than 20 kg and less than or equal to 30 kg and the serum total IgE level of the subject is greater than 1,500 IU/ml and less than or equal to 2,000 IU/ml. In some embodiments, total serum IgE level of the subject is greater than 1,500 IU/ml and less than or equal to 1,850 IU/ml. In some embodiments, the dose of omalizumab is administered to the subject every about 2 weeks.

In some embodiments, the therapeutically effective amount of omalizumab is from about 150 mg to 225 mg, wherein prior to administration to the subject of a first dose of omalizumab, the body weight of the subject is equal to or greater than 10 kg and less than or equal to 15 kg and total serum IgE level of the subject is greater than 600 IU/ml and less than or equal to 2,000 IU/ml. In some embodiments, total serum IgE level of the subject is greater than 600 IU/ml and less than or equal to 1,850 IU/ml. In some embodiments, the dose of omalizumab is administered to the subject every about 2 weeks.

In some embodiments, the therapeutically effective amount of omalizumab is from about 75 mg to 150 mg, wherein prior to administration to the subject of a first dose of omalizumab, the body weight of the subject is greater than 10 kg and less than or equal to 15 kg and the total serum IgE level of the subject is greater than 30 IU/ml and less than or equal to 600 IU/ml. In some embodiments, the dose of omalizumab is administered to the subject every about 4 weeks. In some embodiments, the subject is a child of from 1 year to 4 years of age, from 1 year to 3 years of age, from 1 to 2 years of age, or is about 1 year old.

In some embodiments, the therapeutically effective amount of omalizumab is from about 75 mg to 225 mg, wherein prior to administration to the subject of a first dose of omalizumab, the body weight of the subject is greater than 15 kg and less than or equal to 20 kg and the serum total IgE level of the subject is greater than 30 IU/ml and less than 700 IU/ml. In some embodiments, the dose of omalizumab is administered to the subject every about 4 weeks.

In some embodiments, the therapeutically effective amount of omalizumab is from about 75 mg to 300 mg, wherein prior to administration to the subject of a first dose of omalizumab, the body weight of the subject is greater than 20 kg and less than or equal to 25 kg and the serum total IgE level of the subject is greater than 30 IU/ml and less than 700 IU/ml. In some embodiments, the dose of omalizumab is administered to the subject every about 4 weeks.

In some embodiments, the therapeutically effective amount of omalizumab is from about 75 mg to 300 mg, wherein prior to administration t50 the subject of a first dose of omalizumab, the body weight of the subject is greater than 20 kg and less than or equal to 30 kg and the serum total IgE level of the subject is greater than 30 IU/ml and less than 600 IU/ml. In some embodiments, the dose of omalizumab is administered to the subject every about 4 weeks.

In some embodiments, the therapeutically effective amount of omalizumab is from about 150 mg to 300 mg, wherein prior to administration to the subject of a first dose of omalizumab, the body weight of the subject is greater than 15 kg and less than or equal to 25 kg and the serum total IgE level of the subject is greater than 700 IU/ml and less than 2000 IU/ml. In some embodiments, total serum IgE level of the subject is greater than 600 IU/ml and less than or equal to 1,850 IU/ml. In some embodiments, total serum IgE level of the subject is greater than 600 IU/ml and less than or equal to 1,500 IU/ml. In some embodiments, the dose of omalizumab is administered to the subject every about 2 weeks.

In some embodiments, the therapeutically effective amount of omalizumab is from about 225 mg to 375 mg, wherein prior to administration to the subject of a first dose of omalizumab, the body weight of the subject is greater than 25 kg and less than or equal to 30 kg and the serum total IgE level of the subject is greater than 600 IU/ml and less than 2000 IU/ml. In some embodiments, total serum IgE level of the subject is greater than 600 IU/ml and less than or equal to 1,850 IU/ml. In some embodiments, the dose of omalizumab is administered to the subject every about 2 weeks.

In some embodiments, the therapeutically effective amount of omalizumab is from about 75 mg to 375 mg, wherein prior to administration to the subject of a first dose of omalizumab, the body weight of the subject is equal to or greater than 10 kg and less than or equal to 25 kg, and the total serum IgE level of the subject is equal to or greater than about 30 IU/ml and less than or equal to about 1850 IU/ml. In some embodiments, the dose of omalizumab is administered to the subject every about 2 weeks or 4 weeks. In some embodiments, the age of the subject is from 1 to 4 years.

In some embodiments, the therapeutically effective amount of omalizumab is from about 150 mg to 450 mg, wherein prior to administration to the subject of a first dose of omalizumab, the body weight of the subject is equal to or greater than 10 kg and less than or equal to 30 kg, and the total serum IgE level of the subject is greater than about 1500 IU/ml and less than or equal to about 1850 IU/ml. In some embodiments, the dose of omalizumab is administered to the subject every about 2 weeks.

In some embodiments, the therapeutically effective amount of omalizumab is from 75 mg to 150 mg omalizumab, wherein prior to administration to the subject of a first dose of omalizumab, body weight of the subject is equal to or greater than 10 kg and less than or equal to 15 kg, and total serum IgE level of the subject is equal to or greater than about 30 IU/ml and less than or equal to about 1500 IU/ml. In some embodiments, the dose of omalizumab is administered to the subject every about 2 weeks or 4 weeks.

In some embodiments, the therapeutically effective amount of omalizumab is from 150 mg to 300 mg, wherein prior to administration to the subject of a first dose of omalizumab, the body weight of the subject is equal to or greater than 10 kg and less than or equal to 20 kg, and the total serum IgE level of the subject is equal to or greater than about 30 and less than or equal to about 1850 IU/ml. In some embodiments, the dose of omalizumab is administered to the subject every about 2 weeks.

In some embodiments, the therapeutically effective amount of omalizumab is 75 mg, wherein the body weight of the subject is greater than or equal to 10 kg and less than or equal to 15 kg, and the total serum IgE of the subject is greater than or equal to 30 IU/ml and less than or equal to 300 IU/ml; the body weight of the subject is greater than or equal to 10 kg and less than or equal to 20 kg, and the total serum IgE of the subject is greater than or equal to 30 IU/ml and less than or equal to 200 IU/ml; the body weight of the subject is greater than or equal to 10 kg and less than or equal to 25 kg, and the total serum IgE of the subject is greater than or equal to 30 IU/ml and less than or equal to 100 IU/ml; the body weight of the subject is greater than 15 kg and less than or equal to 20 kg, and the total serum IgE of the subject is greater than or equal to 30 IU/ml and less than or equal to 200 IU/ml; or the body weight of the subject is greater than 20 kg and less than or equal to 25 kg, and the total serum IgE of the subject is greater than or equal to 30 IU/ml and less than or equal to 100 IU/ml; and wherein the dose is administered every 4 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 150 mg, wherein the body weight of the subject is greater than or equal to 10 kg and less than or equal to 12 kg, and the total serum IgE of the subject is greater than 300 IU/ml and less than or equal to 600 IU/ml; the body weight of the subject is greater than 12 kg and less than or equal to 15 kg, and the total serum IgE of the subject is greater than 300 IU/ml and less than or equal to 600 IU/ml; the body weight of the subject is greater than or equal to 10 kg and less than or equal to 15 kg, and the total serum IgE of the subject is greater than 300 IU/ml and less than or equal to 600 IU/ml; the body weight of the subject is greater than 15 kg and less than or equal to 20 kg, and the total serum IgE of the subject is greater than 200 IU/ml and less than or equal to 400 IU/ml; the body weight of the subject is greater than 15 kg and less than or equal to 25 kg, and the total serum IgE of the subject is greater than 200 IU/ml and less than or equal to 300 IU/ml; or the body weight of the subject is greater than 20 kg and less than or equal to 25 kg, and the total serum IgE of the subject is greater than 100 IU/ml and less than or equal to 300 IU/ml; and wherein the dose is administered every 4 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 225 mg, wherein the body weight of the subject is greater than 15 kg and less than or equal to 20 kg, and the total serum IgE of the subject is greater than 400 IU/ml and less than or equal to 700 IU/ml; the body weight of the subject is greater than 15 kg and less than or equal to 25 kg, and the total serum IgE of the subject is greater than 400 IU/ml and less than or equal to 500 IU/ml; or the body weight of the subject is greater than 20 kg and less than or equal to 25 kg, and the total serum IgE of the subject is greater than 300 IU/ml and less than or equal to 500 IU/ml; and wherein the dose is administered every 4 weeks. In some embodiments the body weight of the subject is determined prior to administration of the dose of omalizumab. In some embodiments, the body weight and total serum IgE of the subject are determined prior to administration of a first dose of omalizumab. In some embodiments, the therapeutically effective amount of omalizumab is 300 mg, wherein the body weight of the subject is greater than 20 kg and less than or equal to 25 kg, and the total serum IgE of the subject is greater than 500 IU/ml and less than or equal to 700 IU/ml; and wherein the dose is administered every 4 weeks. In some embodiments the body weight of the subject is determined prior to administration of the dose of omalizumab. In some embodiments, the body weight and total serum IgE of the subject are determined prior to administration of a first dose of omalizumab. In some embodiments, the therapeutically effective amount of omalizumab is 150 mg, wherein the body weight of the subject is greater than or equal to 10 kg and less than or equal to 12 kg, and the total serum IgE of the subject is greater than 600 IU/ml and less than or equal to 1500 IU/ml; the body weight of the subject is greater than 12 kg and less than or equal to 15 kg, and the total serum IgE of the subject is greater than 600 IU/ml and less than or equal to 1200 IU/ml; or the body weight of the subject is greater than 15 kg and less than or equal to 20 kg, and the total serum IgE of the subject is greater than 700 IU/ml and less than or equal to 900 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 225 mg, wherein the body weight of the subject is greater than 12 kg and less than or equal to 15 kg, and the total serum IgE of the subject is greater than 1200 IU/ml and less than or equal to 1850 IU/ml; the body weight of the subject is greater than 15 kg and less than or equal to 20 kg, and the total serum IgE of the subject is greater than 900 IU/ml and less than or equal to 1300 IU/ml; or the body weight of the subject is greater than 20 kg and less than or equal to 25 kg, and the total serum IgE of the subject is greater than 700 IU/ml and less than or equal to 1100 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 300 mg, wherein the body weight of the subject is greater than 15 kg and less than or equal to 20 kg, and the total serum IgE of the subject is greater than 1300 IU/ml and less than or equal to 1850 IU/ml; or the body weight of the subject is greater than 20 kg and less than or equal to 25 kg, and the total serum IgE of the subject is greater than 1100 IU/ml and less than or equal to 1500 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 375 mg, wherein the body weight of the subject is greater than 20 kg and less than or equal to 25 kg, and the total serum IgE of the subject is greater than 1500 IU/ml and less than or equal to 1850 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab. In some embodiments, the therapeutically effective amount of omalizumab is 450 mg, wherein the body weight of the subject is greater than 25 kg and less than or equal to 30 kg, and the total serum IgE of the subject is greater than 1500 IU/ml and less than or equal to 1850 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab.

In some embodiments, the therapeutically effective amount of omalizumab is 600 mg, wherein the body weight of the subject is greater than 30 kg and less than or equal to 40 kg, and the total serum IgE of the subject is greater than 1500 IU/ml and less than or equal to 1850 IU/ml; and wherein the dose is administered every 2 weeks. In some embodiments the body weight of the subject is determined prior to administration of the dose of omalizumab. In some embodiments, the body weight and total serum IgE of the subject are determined prior to administration of a first dose of omalizumab.

In some embodiments, the body weight of the subject is equal to or greater than 10 kg and less than or equal to 12 kg. In some embodiments, the dose is 75 mg, and the dosing frequency is every four weeks when the subject has a baseline total serum IgE of ≥30-100 IU/ml and a body weight of ≥10-12 kg. In some embodiments, the dose is 75 mg, and the dosing frequency is every four weeks when the subject has a baseline total serum IgE of ≥100-200 IU/ml and a body weight of ≥10-12 kg. In some embodiments, the dose is 75 mg, and the dosing frequency is every four weeks when the subject has a baseline total serum IgE of >200-300 IU/ml and a body weight of ≥10-12 kg. In some embodiments, the dose is 150 mg, and the dosing frequency is every four weeks when the subject has a baseline total serum IgE of >300-400 IU/ml and a body weight of ≥10-12 kg. In some embodiments, the dose is 150 mg, and the dosing frequency is every four weeks when the subject has a baseline total serum IgE of >400-500 IU/ml and a body weight of ≥10-12 kg. In some embodiments, the dose is 150 mg, and the dosing frequency is every four weeks when the subject has a baseline total serum IgE of >500-600 IU/ml and a body weight of ≥10-12 kg. In some embodiments, the dose is 150 mg, and the dosing frequency is every two weeks when the subject has a baseline total serum IgE of >600-700 IU/ml and a body weight of ≥10-12 kg. In some embodiments, the dose is 150 mg, and the dosing frequency is every two weeks when the subject has a baseline total serum IgE of >700-800 IU/ml and a body weight of ≥10-12 kg. In some embodiments, the dose is 150 mg, and the dosing frequency is every two weeks when the subject has a baseline total serum IgE of >800-900 IU/ml and a body weight of ≥10-12 kg. In some embodiments, the dose is 150 mg, and the dosing frequency is every two weeks when the subject has a baseline total serum IgE of >900-1000 IU/ml and a body weight of ≥10-12 kg. In some embodiments, the dose is 150 mg, and the dosing frequency is every two weeks when the subject has a baseline total serum IgE of ≥1000-1100 IU/ml and a body weight of ≥10-12 kg. In some embodiments, the dose is 150 mg, and the dosing frequency is every two weeks when the subject has a baseline total serum IgE of >1100-1200 IU/ml and a body weight of ≥10-12 kg. In some embodiments, the dose is 150 mg, and the dosing frequency is every two weeks when the subject has a baseline total serum IgE of >1200-1300 IU/ml and a body weight of ≥10-12 kg. In some embodiments, the dose is 150 mg, and the dosing frequency is every two weeks when the subject has a baseline total serum IgE of >1300-1500 IU/ml and a body weight of ≥10-12 kg. In some embodiments, the subject is not dosed when the subject has a baseline total serum IgE of or >1500-1850 IU/ml or >1500-1850 IU/ml and a body weight of ≥10-12 kg.

In some embodiments, the body weight of the subject is greater than 12 kg and less than or equal to 15 kg. In some embodiments, the dose is 75 mg, and the dosing frequency is every four weeks when the subject has a baseline total serum IgE of ≥30-100 IU/ml and a body weight of >12-15 kg. In some embodiments, the dose is 75 mg, and the dosing frequency is every four weeks when the subject has a baseline total serum IgE of >100-200 IU/ml and a body weight of >12-15 kg. In some embodiments, the dose is 75 mg, and the dosing frequency is every four weeks when the subject has a baseline total serum IgE of >200-300 IU/ml and a body weight of >12-15 kg. In some embodiments, the dose is 150 mg, and the dosing frequency is every four weeks when the subject has a baseline total serum IgE of >300-400 IU/ml and a body weight of >12-15 kg. In some embodiments, the dose is 150 mg, and the dosing frequency is every four weeks when the subject has a baseline total serum IgE of >400-500 IU/ml and a body weight of >12-15 kg. In some embodiments, the dose is 150 mg, and the dosing frequency is every four weeks when the subject has a baseline total serum IgE of >500-600 IU/ml and a body weight of >12-15 kg. In some embodiments, the dose is 150 mg, and the dosing frequency is every two weeks when the subject has a baseline total serum IgE of >600-700 IU/ml and a body weight of >12-15 kg. In some embodiments, the dose is 150 mg, and the dosing frequency is every two weeks when the subject has a baseline total serum IgE of >700-800 IU/ml and a body weight of >12-15 kg. In some embodiments, the dose is 150 mg, and the dosing frequency is every two weeks when the subject has a baseline total serum IgE of >800-900 IU/ml and a body weight of >12-15 kg. In some embodiments, the dose is 150 mg, and the dosing frequency is every two weeks when the subject has a baseline total serum IgE of >900-1000 IU/ml and a body weight of >12-15 kg. In some embodiments, the dose is 150 mg, and the dosing frequency is every two weeks when the subject has a baseline total serum IgE of >1000-1100 IU/ml and a body weight of >12-15 kg. In some embodiments, the dose is 150 mg, and the dosing frequency is every two weeks when the subject has a baseline total serum IgE of >1100-1200 IU/ml and a body weight of >12-15 kg. In some embodiments, the dose is 225 mg, and the dosing frequency is every two weeks when the subject has a baseline total serum IgE of >1200-1300 IU/ml and a body weight of >12-15 kg. In some embodiments, the dose is 225 mg, and the dosing frequency is every two weeks when the subject has a baseline total serum IgE of >1300-1500 IU/ml and a body weight of >12-15 kg. In some embodiments, the dose is 225 mg, and the dosing frequency is every two weeks when the subject has a baseline total serum IgE of or >1500-1850 IU/ml or >1500-1850 IU/ml and a body weight of >12-15 kg.

In some embodiments, the body weight of the subject is greater than 15 kg and less than or equal to 20 kg. In some embodiments, the dose is 75 mg, and the dosing frequency is every four weeks when the subject has a baseline total serum IgE of >30-100 IU/ml and a body weight of >15-20 kg. In some embodiments, the dose is 75 mg, and the dosing frequency is every four weeks when the subject has a baseline total serum IgE of >100-200 IU/ml and a body weight of >15-20 kg. In some embodiments, the dose is 150 mg, and the dosing frequency is every four weeks when the subject has a baseline total serum IgE of >200-300 IU/ml and a body weight of >15-20 kg. In some embodiments, the dose is 150 mg, and the dosing frequency is every four weeks when the subject has a baseline total serum IgE of >300-400 IU/ml and a body weight of >15-20 kg. In some embodiments, the dose is 225 mg, and the dosing frequency is every four weeks when the subject has a baseline total serum IgE of >400-500 IU/ml and a body weight of >15-20 kg. In some embodiments, the dose is 225 mg, and the dosing frequency is every four weeks when the subject has a baseline total serum IgE of >500-600 IU/ml and a body weight of >15-20 kg. In some embodiments, the dose is 225 mg, and the dosing frequency is every four weeks when the subject has a baseline total serum IgE of >600-700 IU/ml and a body weight of >15-20 kg. In some embodiments, the dose is 150 mg, and the dosing frequency is every two weeks when the subject has a baseline total serum IgE of >700-800 IU/ml and a body weight of >15-20 kg. In some embodiments, the dose is 150 mg, and the dosing frequency is every two weeks when the subject has a baseline total serum IgE of >800-900 IU/ml and a body weight of >15-20 kg. In some embodiments, the dose is 225 mg, and the dosing frequency is every two weeks when the subject has a baseline total serum IgE of >900-1000 IU/ml and a body weight of >15-20 kg. In some embodiments, the dose is 225 mg, and the dosing frequency is every two weeks when the subject has a baseline total serum IgE of >1000-1100 IU/ml and a body weight of >15-20 kg. In some embodiments, the dose is 225 mg, and the dosing frequency is every two weeks when the subject has a baseline total serum IgE of >1100-1200 IU/ml and a body weight of >15-20 kg. In some embodiments, the dose is 225 mg, and the dosing frequency is every two weeks when the subject has a baseline total serum IgE of >1200-1300 IU/ml and a body weight of >15-20 kg. In some embodiments, the dose is 300 mg, and the dosing frequency is every two weeks when the subject has a baseline total serum IgE of >1300-1500 IU/ml and a body weight of >15-20 kg. In some embodiments, the dose is 300 mg, and the dosing frequency is every two weeks when the subject has a baseline total serum IgE of or >1500-2000 IU/ml >1500-1850 IU/ml and a body weight of >15-20 kg.

In some embodiments, the body weight of the subject is greater than 20 kg and less than or equal to 25 kg. In some embodiments, the dose is 75 mg, and the dosing frequency is every four weeks when the subject has a baseline total serum IgE of >30-100 IU/ml and a body weight of >20-25 kg. In some embodiments, the dose is 150 mg, and the dosing frequency is every four weeks when the subject has a baseline total serum IgE of >100-200 IU/ml and a body weight of >20-25 kg. In some embodiments, the dose is 150 mg, and the dosing frequency is every four weeks when the subject has a baseline total serum IgE of >200-300 IU/ml and a body weight of >20-25 kg. In some embodiments, the dose is 225 mg, and the dosing frequency is every four weeks when the subject has a baseline total serum IgE of >300-400 IU/ml and a body weight of >20-25 kg. In some embodiments, the dose is 225 mg, and the dosing frequency is every four weeks when the subject has a baseline total serum IgE of >400-500 IU/ml and a body weight of >20-25 kg. In some embodiments, the dose is 300 mg, and the dosing frequency is every four weeks when the subject has a baseline total serum IgE of >500-600 IU/ml and a body weight of >20-25 kg. In some embodiments, the dose is 300 mg, and the dosing frequency is every four weeks when the subject has a baseline total serum IgE of >600-700 IU/ml and a body weight of >20-25 kg. In some embodiments, the dose is 225 mg, and the dosing frequency is every two weeks when the subject has a baseline total serum IgE of >700-800 IU/ml and a body weight of >20-25 kg. In some embodiments, the dose is 225 mg, and the dosing frequency is every two weeks when the subject has a baseline total serum IgE of >800-900 IU/ml and a body weight of >20-25 kg. In some embodiments, the dose is 225 mg, and the dosing frequency is every two weeks when the subject has a baseline total serum IgE of >900-1000 IU/ml and a body weight of >20-25 kg. In some embodiments, the dose is 225 mg, and the dosing frequency is every two weeks when the subject has a baseline total serum IgE of >1000-1100 IU/ml and a body weight of >20-25 kg. In some embodiments, the dose is 300 mg, and the dosing frequency is every two weeks when the subject has a baseline total serum IgE of >1100-1200 IU/ml and a body weight of >20-25 kg. In some embodiments, the dose is 300 mg, and the dosing frequency is every two weeks when the subject has a baseline total serum IgE of >1200-1300 IU/ml and a body weight of >20-25 kg. In some embodiments, the dose is 300 mg, and the dosing frequency is every two weeks when the subject has a baseline total serum IgE of >1300-1500 IU/ml and a body weight of >20-25 kg. In some embodiments, the dose is 375 mg, and the dosing frequency is every two weeks when the subject has a baseline total serum IgE of >1500-1850 IU/ml or >1500-1850 IU/ml and a body weight of >20-25 kg.

In some embodiments, the body weight of the subject is greater than 25 kg and less than or equal to 30 kg. In some embodiments, the dose is 450 mg, and the dosing frequency is every two weeks when the subject has a baseline total serum IgE of >1500-2000 IU/ml or >1500-1850 IU/ml and a body weight of >25-30 kg.

iii. Route and Duration of Administration

The pharmaceutical compositions of the present disclosure comprising an anti-IgE antibody, such as omalizumab, are administered by subcutaneous injection to a human subject diagnosed with or suffering from one or more food allergies.

The methods of the present disclosure may include repeated administration of the pharmaceutical composition comprising an anti-IgE antibody, such as omalizumab. In some embodiments, the duration of administration is until the subject is no longer diagnosed with food allergy. In some embodiments, the duration of treating is at least 16 to 20 weeks in length. In some embodiments, the duration of treating is at least 40 to 48 weeks in length. In some embodiments, the duration of treating is at least about 10 months to about 12 months in length. For example, in some embodiments, the duration of treating can be at least about 16 weeks, 18 weeks, 20 weeks, 22 weeks, 24 weeks, 26 weeks, 28 weeks, 30 weeks, 32 weeks, 34 weeks, 36 weeks, 38 weeks, or 40 weeks. In some embodiments, the duration of treating can be at least about 6 months, 8 months, about 10 months, or 12 months.

B. Kits

The present disclosure also provides kits for use in the methods described above. In some embodiments, the kits, comprise: i) a pharmaceutical composition comprising an anti-IgE antibody, such as omalizumab; and ii) instructions for administration of the pharmaceutical composition by subcutaneous injection to a human subject suffering from one or more food antibodies to prevent an allergic reaction triggerable by consumption of a food allergen by the human subject, wherein the pharmaceutical composition is administered at an anti-IgE antibody (e.g., omalizumab) dose and a dosing interval determined from measurement of body weight and baseline total serum IgE level of the subject. In some embodiments, the pharmaceutical composition is an aqueous solution further comprising L-arginine hydrochloride, L-histidine, and L-histidine hydrochloride monohydrate. In some embodiments, the pharmaceutical composition further comprises sucrose. In specific embodiments, the pharmaceutical composition contains omalizumab at a concentration of about 150 g/L in 0.02 M histidine, 0.2 M arginine-HCl, and 0.04% polysorbate 20, pH 6. In some embodiments, the pharmaceutical composition is present in a pre-filled syringe. In some embodiments, the pharmaceutical composition is a lyophilized powder present in a vial, and the kit further comprises instructions for reconstituting the lyophilized powder in water for injection.

III. Enumerated Embodiments

1. A method of treating a human subject diagnosed with a food allergy to one or more food allergens, the method comprising:
   administering by subcutaneous injection to the subject once about every two weeks a pharmaceutical composition comprising omalizumab at a dose of from 150 mg to 300 mg,
   wherein prior to administration of a first dose of omalizumab to the subject, body weight of the subject is equal to or greater than 10 kg and less than or equal to 20 kg and total serum IgE level of the subject is greater than 600 IU/ml and less than or equal to 2,000 IU/ml.
2. The method of embodiment 1, wherein the dose of omalizumab administered about every two weeks is:
   150 mg when the body weight of the subject is equal to or greater than 10 kg and less than or equal to 12 kg and the total serum IgE level of the subject is greater than 600 IU/ml and less than or equal to 2,000 IU/ml; or
   150 mg when the body weight of the subject is greater than 12 kg and less than or equal to 15 kg and the total serum IgE level of the subject is greater than 600 IU/ml and less than or equal to 1200 IU/ml; or
   150 mg when the body weight of the subject is greater than 15 kg and less than or equal to 20 kg and the total serum IgE level of the subject is greater than 700 IU/ml and less than or equal to 900 IU/ml.
3. The method of embodiment 1, wherein the dose of omalizumab administered about every two weeks is:
   225 mg when the body weight of the subject is greater than 12 kg and less than or equal to 15 kg and the total serum IgE level of the subject is greater than 1200 IU/ml and less than or equal to 2000 IU/ml; or
   225 mg when the body weight of the subject is greater than 15 kg and less than or equal to 20 kg and the total serum IgE level of the subject is greater than 900 IU/ml and less than or equal to 1300 IU/ml.
4. The method of embodiment 1, wherein the dose of omalizumab administered about every two weeks is:
   300 mg when the body weight of the subject is greater than 15 kg and less than or equal to 20 kg and the total serum IgE level of the subject is greater than 1300 IU/ml and less than or equal to 2000 IU/ml.
5. The method of any one of embodiments 1-5, wherein the subject is from 1 year to 5 years of age, optionally wherein the subject is from about 1 year to 4 years of age, or from about 1 year to 3 years of age, or about 1 year or about 2 years of age.
6. A method of treating a human subject diagnosed with a food allergy to one or more food allergens, the method comprising:
   administering by subcutaneous injection to the subject once about every two weeks a pharmaceutical composition comprising omalizumab at a dose of from 375 mg to 450 mg,
   wherein prior to administration of a first dose of omalizumab to the subject, body weight of the subject is greater than 20 kg and less than or equal to 30 kg and total serum IgE level of the subject is greater than 1,500 IU/ml and less than or equal to 2,000 IU/ml.
7. The method of embodiment 6, wherein the body weight of the subject is greater than 20 kg and less than or equal to 25 kg.
8. The method of embodiment 7, wherein the dose of omalizumab administered about every two weeks is 375 mg.
9. The method of embodiment 6, wherein the body weight of the subject is greater than 25 kg and less than or equal to 30 kg.
10. The method of embodiment 9, wherein the dose of omalizumab administered about every two weeks is 450 mg.
11. A method of treating a human subject diagnosed with a food allergy to one or more food allergens, the method comprising:
    administering by subcutaneous injection to the subject once about every two weeks a pharmaceutical composition comprising omalizumab at a dose of from 150 mg to 225 mg,
    wherein prior to administration of a first dose of omalizumab to the subject, body weight of the subject is equal to or greater than 10 kg and less than or equal to 15 kg and total serum IgE level of the subject is greater than 600 IU/ml and less than or equal to 2,000 IU/ml.
12. The method of embodiment 11, wherein the body weight of the subject is equal to or greater than 10 kg and less than or equal to 12 kg.
13. The method of embodiment 12, wherein the dose of omalizumab administered about every two weeks is 150 mg.

14. The method of embodiment 13, wherein the total serum IgE level of the subject is greater than 700 IU/ml and less than or equal to 1,500 IU/ml.
15. The method of embodiment 11, wherein the body weight of the subject is greater than 12 kg and less than or equal to 15 kg.
16. The method of embodiment 15, wherein the dose of omalizumab administered about every two weeks is 150 mg when the total serum IgE level of the subject is greater than 600 IU/ml and less than or equal to 1,200 IU/ml.
17. The method of embodiment 16, wherein the total serum IgE level of the subject is greater than 700 IU/ml and less than or equal to 1,200 IU/ml.
18. The method of embodiment 15, wherein the dose of omalizumab administered about every two weeks is 225 mg when the total serum IgE level of the subject is greater than 1,200 IU/ml and less than or equal to 2,000 IU/ml.
19. The method of any one of embodiments 11-18, wherein the subject is from 1 year to 5 years of age.
20. The method of embodiment 19, wherein the subject is from 1 year to 4 years of age, optionally wherein the subject is from 1 year to 3 years of age.
21. A method of treating a human subject diagnosed with o food allergy to one or more food allergens, the method comprising:
   administering by subcutaneous injection to the subject once about every four weeks a pharmaceutical composition comprising omalizumab at a dose of from 75 mg to 150 mg,
   wherein prior to administration of a first dose of omalizumab to the subject, body weight of the subject is equal to or greater than 10 kg and less than or equal to 15 kg and total serum IgE level of the subject is equal to or greater than 30 IU/ml and less than or equal to 600 IU/ml.
22. The method of embodiment 21, wherein the body weight of the subject is equal to or greater than 10 kg and less than or equal to 12 kg.
23. The method of embodiment 22, wherein the dose of omalizumab administered once about every four weeks is 75 mg when the total serum IgE level of the subject is equal to or greater than 30 IU/ml and less than or equal to 300 IU/ml.
24. The method of embodiment 22, wherein the dose of omalizumab administered once about every four weeks is 150 mg when the total serum IgE level of the subject is greater than 300 IU/ml and less than or equal to 600 IU/ml.
25. The method of embodiment 21, wherein the body weight of the subject is greater than 12 kg and less than or equal to 15 kg.
26. The method of embodiment 25, wherein the dose of omalizumab administered once about every four weeks is 75 mg when the total serum IgE level of the subject is equal to or greater than 30 IU/ml and less than or equal to 300 IU/ml.
27. The method of embodiment 25, wherein the dose of omalizumab administered once about every four weeks is 150 mg when the total serum IgE level of the subject is greater than 300 IU/ml and less than or equal to 600 IU/ml.
28. A method of treating a human subject diagnosed with a food allergy to one or more food allergens, the method comprising:
   administering by subcutaneous injection to the subject once about every two weeks a pharmaceutical composition comprising a therapeutically effective amount omalizumab,
   wherein prior to administration of a first dose of omalizumab to the subject, body weight of the subject is equal to or greater than 10 kg and less than or equal to 15 kg.
29. A method of treating a human subject diagnosed with a food allergy to one or more food allergens, the method comprising:
   administering by subcutaneous injection to the subject once about every two to four weeks a pharmaceutical composition comprising a therapeutically effective amount omalizumab,
   wherein prior to administration of a first dose of omalizumab to the subject, body weight of the subject is equal to or greater than 10 kg and less than or equal to 25 kg.
30. The method of embodiment 28 or embodiment 29, wherein the body weight of the subject is equal to or greater than 10 kg and less than or equal to 12 kg.
31. The method of embodiment 28 or embodiment 29, wherein the body weight of the subject is greater than 12 kg and less than or equal to 15 kg.
32. The method of embodiment 29, wherein the body weight of the subject is greater than 15 kg and less than or equal to 20 kg.
33. The method of embodiment 29, wherein the body weight of the subject is greater than 20 kg and less than or equal to 25 kg.
34. The method of embodiment 30 or embodiment 31, wherein total serum IgE level of the subject prior to administration of the first dose of omalizumab is greater than 600 IU/ml and less than or equal to 2,000 IU/ml.
35. The method of any one of embodiments 30-33, wherein the total serum IgE level of the subject prior to administration of the first dose of omalizumab is greater than 1,500 IU/ml and less than or equal to 1,850 IU/ml.
36. The method of any one of embodiments 1-35, wherein the subject has not been diagnosed with allergic rhinoconjunctivitis prior to administration of the first dose of omalizumab.
37. The method of any one of embodiments 1-36, wherein the subject has not been diagnosed with asthma, nasal polyps, or chronic spontaneous urticaria prior to administration of the first dose of omalizumab.
38. The method of any one of embodiments 1-37, wherein the food allergy comprises an allergy to one or more food allergens selected from the group consisting of peanut, milk, egg, wheat, cashew, hazelnut, or walnut, and a combination thereof.
39. The method of embodiment 38, wherein the food allergy comprises an allergy to two or more food allergens selected from the group consisting of peanut, milk, egg, wheat, cashew, hazelnut, or walnut, and a combination thereof.
40. The method of embodiment 38, wherein the food allergy comprises an allergy to peanut and an allergy to two or more food allergens selected from milk, egg, wheat, cashew, hazelnut and walnut.
41. The method of embodiment 40, wherein the subject was identified as having food allergy to multiple food allergens prior to the administering step according to criteria comprising:

a) a skin-prick test resulting in a wheal of at least 4 mm in diameter to peanut and two or more of milk, egg, wheat, cashew, hazelnut and walnut; and/or b) a peanut IgE level of at least 6 kUA/L and an IgE level of at least 6 kUA/L to two or more allergens selected from milk, egg, wheat, cashew, hazelnut and walnut; and/or c) development of a moderate-to-severe allergic reaction after consumption of about 100 mg or from 10 mg to 100 mg of peanut protein, and/or consumption of about 300 mg or from 30 mg to 300 mg of milk, egg, wheat, cashew, hazelnut and/or walnut protein.

42. The method of any one of embodiments 1-40, wherein the allergic reaction is a moderate-to-severe allergic reaction.

43. The method of embodiment 42, wherein the moderate-to-severe allergic reaction to a food comprises onset of one or more symptoms after consumption of about 100 mg or from 10 mg to 100 mg of peanut protein, and/or consumption of about 300 mg or from 30 mg to 300 mg of milk, egg, wheat, cashew, hazelnut and/or walnut protein, and wherein the one or more symptoms comprise one or more:

skin: systemic hives, more than mild lip or face edema, pruritus causing protracted scratching, several areas of erythema pronounced erythema, and combinations thereof; and/or respiratory: throat tightness with or without hoarseness, persistent cough, wheezing with or without dyspnea, laryngeal edema, stridor, and combinations thereof; and/or gastrointestinal tract: moderate to severe abdominal pain, cramping, nausea, vomiting, and combinations thereof; and/or neurological: change in mental status; and/or circulatory: hypotension.

44. The method of any one of embodiments 1-43, wherein preventing the allergic reaction permits the subject to consume a single dose of about 600 mg or from 600 mg to 1800 mg of peanut protein, and/or a single dose of about 1000 mg or from 1000 mg to 3000 mg of milk, egg, wheat, cashew, hazelnut and/or walnut protein without triggering dose-limiting symptoms.

45. The method of any one of embodiments 1-43, wherein preventing the allergic reaction permits the subject to consume a single dose of about 1000 mg or from 1000 mg to 3000 mg of peanut, milk, egg, wheat, cashew, hazelnut and/or walnut protein without triggering dose-limiting symptoms.

46. The method of any one of embodiments 1-43, wherein preventing the allergic reaction permits the subject to consume a single dose of about 2000 mg or from 2000 mg to 6000 mg of peanut, milk, egg, wheat, cashew, hazelnut and/or walnut protein without triggering dose-limiting symptoms.

47. The method of any one of embodiments 1-43, wherein preventing the allergic reaction reduces likelihood that the subject will require treatment with antihistamine or epinephrine after consuming a single dose of about 100 mg or from 100 mg to 300 mg of peanut protein, and/or a single dose of about 300 mg or from 300 mg to 900 mg of milk, egg, wheat, cashew, hazelnut and/or walnut protein.

48. The method of any one of embodiments 1-47, further comprising determining the body weight and the total serum IgE level of the subject prior to administration of the first dose of omalizumab.

49. The method of embodiment 48, wherein determining the body weight and the total serum IgE level of the subject is done one within month prior to administration of the first dose of omalizumab.

50. The method of embodiment 49, wherein determining the body weight and the total serum IgE level of the subject is done two weeks prior to administration of the first dose of omalizumab.

51. The method of any one of embodiments 1-50, wherein duration of the administering step is at least 16 to 20 weeks in length.

52. The method of any one of embodiments 1-50, wherein duration of the administering step is at least 10 to 12 months in length.

53. The method of any one of embodiments 48-52, wherein determining the total serum IgE level is done with an enzyme-linked immunosorbent assay.

54. The method of any one of embodiments 1-53, wherein the pharmaceutical composition is an aqueous solution further comprising L-arginine hydrochloride, L-histidine, and L-histidine hydrochloride monohydrate.

55. The method of embodiment 54, wherein the pharmaceutical composition further comprises sucrose.

56. The method of any one of embodiments 1-55, wherein the method prevents or reduces allergic reaction in the subject following consumption of food containing the one or more food allergens.

57. The method of any one of embodiments 1-56, wherein the method does not comprise concurrent oral immunotherapy with the one or more food allergens.

58. A kit comprising:

i) a pharmaceutical composition comprising omalizumab; and ii) instructions for administering the pharmaceutical composition according to the method of any one of embodiments 1-57.

59. The kit of embodiment 58, wherein the pharmaceutical composition is an aqueous solution present in a prefilled syringe.

60. The kit of embodiment 58, wherein the pharmaceutical composition is lyophilized powder present in a vial and the kit further comprises sterile water for injection and instructions for reconstitution of the powder with the sterile water.

61. The kit of embodiment 60, wherein the kit further comprises a syringe and a needle for subcutaneous injection of the pharmaceutical composition.

62. Omalizumab for use in a method of treating a human subject diagnosed with a food allergy to one or more food allergens, the method comprising:

administering by subcutaneous injection once every two weeks to the subject a pharmaceutical composition comprising omalizumab at a dose of from 150 mg to 300 mg, wherein prior to administration of a first dose of omalizumab to the subject, body weight of the subject is equal to or greater than 10 kg and less than or equal to 20 kg and total serum IgE level of the subject is greater than 600 IU/ml and less than or equal to 2,000 IU/ml, and wherein the method does not comprise concurrent oral immunotherapy with the food allergen.

63. Omalizumab for use in a method of treating a human subject diagnosed with a food allergy to one or more food allergens, the method comprising:

administering by subcutaneous injection once every two weeks to the subject a pharmaceutical composition comprising omalizumab at a dose of from 375 mg to 450 mg, wherein prior to administration of a first dose of omalizumab to the subject, body weight of the subject is equal to or greater than 20 kg and less than or equal to 30 kg and total serum IgE level of the subject is greater than 1,500 IU/ml and less than or equal to 2,000 IU/ml, and wherein the method does not comprise concurrent oral immunotherapy with the food allergen.

64. Omalizumab for use in a method of treating a human subject diagnosed with a food allergy to one or more food allergens, the method comprising:

administering by subcutaneous injection once every two weeks to the subject a pharmaceutical composition comprising omalizumab at a dose of from 150 mg to 225 mg, wherein prior to administration of a first dose of omalizumab to the subject, body weight of the subject is equal to or greater than 10 kg and less than or equal to 15 kg and total serum IgE level of the subject is greater than 600 IU/ml and less than or equal to 2,000 IU/ml, and wherein the method does not comprise concurrent oral immunotherapy with the food allergen.

65. Omalizumab for use in a method of treating a human subject diagnosed with a food allergy to one or more food allergens, the method comprising:

administering by subcutaneous injection once every four weeks to the subject a pharmaceutical composition comprising omalizumab at a dose of from 75 mg to 150 mg, wherein prior to administration of a first dose of omalizumab to the subject, body weight of the subject is equal to or greater than 10 kg and less than or equal to 15 kg and total serum IgE level of the subject is equal to or greater than 30 IU/ml and less than or equal to 600 IU/ml, and wherein the method does not comprise concurrent oral immunotherapy with the food allergen.

66. Use of omalizumab at a dose of from 150 mg to 300 mg in the manufacture of a medicament for treating a human subject diagnosed with a food allergy to one or more food allergens, wherein the medicament is to be administered by subcutaneous injection once every two weeks to the subject when prior to administration of a first dose of omalizumab to the subject, body weight of the subject is equal to or greater than 10 kg and less than or equal to 20 kg and total serum IgE level of the subject is greater than 600 IU/ml and less than or equal to 2,000 IU/ml, and wherein the medicament is not administered in combination with oral immunotherapy with the food allergen.

67. Use of omalizumab at a dose of from 375 mg to 450 mg in the manufacture of a medicament for treating a human subject diagnosed with a food allergy to one or more food allergens, wherein the medicament is to be administered by subcutaneous injection once every two weeks to the subject when prior to administration of a first dose of omalizumab to the subject, body weight of the subject is equal to or greater than 20 kg and less than or equal to 30 kg and total serum IgE level of the subject is greater than 1,500 IU/ml and less than or equal to 2,000 IU/ml, and wherein the medicament is not administered in combination with oral immunotherapy with the food allergen.

68. Use of omalizumab at a dose of from 150 mg to 225 mg in the manufacture of a medicament for treating a human subject diagnosed with a food allergy to one or more food allergens, wherein the medicament is to be administered by subcutaneous injection once every two weeks to the subject when prior to administration of a first dose of omalizumab to the subject, body weight of the subject is equal to or greater than 10 kg and less than or equal to 15 kg and total serum IgE level of the subject is greater than 600 IU/ml and less than or equal to 2,000 IU/ml, and wherein the medicament is not administered in combination with oral immunotherapy with the food allergen.

69. Use of omalizumab at a dose of from 75 mg to 150 mg in the manufacture of a medicament for treating a human subject diagnosed with a food allergy to one or more food allergens, wherein the medicament is to be administered by subcutaneous injection once every four weeks to the subject when prior to administration of a first dose of omalizumab to the subject, body weight of the subject is equal to or greater than 10 kg and less than or equal to 15 kg and total serum IgE level of the subject is equal to or greater than 30 IU/ml and less than or equal to 600 IU/ml, and wherein the medicament is not administered in combination with oral immunotherapy with the food allergen.

70. A method of treating a human subject diagnosed with a food allergy to one or more food allergens selected from the group consisting of peanut, cashew, milk and egg proteins, the method comprising administering to the human subject as effective amount of omalizumab by subcutaneous injection once every two or four weeks, wherein administering omalizumab to a plurality of human subjects in the absence of oral immunotherapy results in an odds ratio (OR) of at least about 3 for preventing development of dose-limiting symptoms after the human subjects consume a single dose of about 600 mg of peanut protein, and/or a single dose of about 1000 mg of cashew protein, and/or a single dose of about 1000 mg milk protein, and/or a single dose of about 1000 mg egg protein, optionally wherein the OR is from about 3 to about 900, or wherein the OR is from about 15 to about 45.

71. The method of embodiment 70, wherein the plurality of human subjects have a food allergy to peanut protein, and wherein administering omalizumab to a plurality of human subjects in the absence of oral immunotherapy results in an odds ratio (OR) of from about 10 to about 200 for preventing development of dose-limiting symptoms after the human subjects consume a single dose of about 600 mg of peanut protein, optionally wherein the OR is from about 30 to about 40, or wherein the OR is about 37.

72. The method of embodiment 70, wherein the plurality of human subjects have a food allergy to cashew protein, and wherein administering omalizumab to a plurality of human subjects in the absence of oral immunotherapy results in an odds ratio (OR) of from about 3 to about 900 for preventing development of dose-limiting symptoms after the human subjects consume a single dose of about 1000 mg of cashew protein, optionally wherein the OR is from about 15 to about 25, or wherein the OR is about 21.

73. The method of embodiment 70, wherein the plurality of human subjects have a food allergy to milk protein, and wherein administering omalizumab to a plurality of human subjects in the absence of oral immunotherapy results in an odds ratio (OR) of from about 3 to about 160 for preventing development of dose-limiting symptoms after the human subjects consume a single dose of about 1000 mg of milk protein, optionally wherein the OR is from about 10 to about 20, or wherein the OR is about 16.
74. The method of embodiment 70, wherein the plurality of human subjects have a food allergy to egg protein, and wherein administering omalizumab to a plurality of human subjects in the absence of oral immunotherapy results in an odds ratio (OR) of at least about 10 for preventing development of dose-limiting symptoms after the human subjects consume a single dose of about 1000 mg of egg protein, optionally wherein the OR is at least about 100, 1,000, 10,000, 100,000, or 1,000,000.
75. A method of treating a human subject diagnosed with a food allergy to one or more food allergens, the method comprising:
    administering to the subject an anti-IgE antibody at a dose of from 75 mg to 300 mg,
    wherein the subject has a body weight equal to or greater than about 10 kg and less than or equal to about 20 kg, and the subject has a total serum IgE level equal to or greater than about 30 IU/ml.
76. The method of embodiment 75, wherein the anti-IgE antibody is omalizumab.
77. The method of embodiment 75, wherein the omalizumab is administered as a pharmaceutical composition comprising omalizumab.
78. The method of any one of embodiments 75 to 77, wherein the subject has a total serum IgE level equal to or greater than about 30 IU/ml and less than or equal to about 2,000 IU/ml.
79. The method of any one of embodiments 75 to 78, wherein each dose of anti-IgE antibody administered to the subject is determined prior to administration of the first dose of the anti-IgE antibody.
80. The method of any one of embodiments 75 to 79, wherein the subject has a total serum IgE level of equal to or greater than about 30 IU/ml and less than or equal to about 2,000 IU/ml prior to administration of the first dose of the anti-IgE antibody.
81. The method any one of embodiments 75 to 80, wherein the subject has a body weight equal to or greater than about 10 kg and less than or equal to about 20 kg prior to administration of the first dose of the anti-IgE antibody.
82. The method of any one of embodiments 75 to 81, wherein the dose of anti-IgE antibody is administered to the subject every two or four weeks.
83. The method of any one of embodiments 75 to 82, wherein the dose of anti-IgE antibody is (i) 75 mg every 4 weeks if the subject has
    a body weight of ≥10-15 kg, and total serum IgE level of ≥30-300 IU/ml, or
    a body weight of ≥10-20 kg, and total serum IgE level of ≥30-200 IU/ml;

(ii) 150 mg every 4 weeks if the subject has
    a body weight of ≥10-15 kg, and total serum IgE level of >300-600 IU/ml,
    a body weight of ≥10-20 kg, and total serum IgE level of >300-400 IU/ml, or
    a body weight of >15-20 kg, and total serum IgE level of >200-400 IU/ml;

(iii) 225 mg every 4 weeks if the subject has
    a body weight of >15-20 kg, and total serum IgE level of >400-700 IU/ml;

(iv) 150 mg every 2 weeks if the subject has
    a body weight of ≥10-12 kg, and total serum IgE level of >600-1500 IU/ml,
    a body weight of >12-15 kg, and total serum IgE level of >600-1200 IU/ml,
    a body weight of ≥10-15 kg, and total serum IgE level of >600-1200 IU/ml, or
    a body weight of ≥10-20 kg, and total serum IgE level of >700-900 IU/ml;

(v) 225 mg every 2 weeks if the subject has
    a body weight of >12-15 kg, and total serum IgE level of >1200-1850 IU/ml, or
    a body weight of >15-20 kg, and total serum IgE level of >900-1300 IU/ml; and (vi) 300 mg every 2 weeks if the subject has
    a body weight of >15-20 kg, and total serum IgE level of >1300-1850 IU/ml.

84. The method of any one of embodiments 75 to 83, wherein the dose of anti-IgE antibody is administered to the subject subcutaneously or intravenously.
85. The method of embodiment 84, wherein the dose of anti-IgE antibody is administered to the subject subcutaneously.
86. The method of embodiment 85, wherein the dose of anti-IgE antibody is administered to the subject by subcutaneous injection.
87. The method of any one of embodiments 75 to 86, wherein the dose of anti-IgE antibody is administered to the subject until said subject is no longer diagnosed with food allergy.
88. The method of any one of embodiments 75 to 87, wherein the subject is diagnosed with food allergy to more than one food allergen.
89. The method of any one of embodiments 75 to 88, wherein the food allergen comprises peanut protein.
90. The method of any one of embodiments 75 to 89, wherein the subject is greater than 1 year and less than 6 years of age.
91. The method of any one of embodiments 75 to 90, wherein the dose of anti-IgE antibody is not administered in combination with oral immunotherapy with the food allergen.
92. The method any one of embodiments 75 to 91, wherein the incidence of allergic reaction to the food allergen is reduced.
93. The method any one of embodiments 75 to 91, wherein the severity of allergic reaction to the food allergen is reduced.
94. The method any one of embodiments 75 to 91, wherein allergic reaction to the food allergen is prevented.

EXAMPLES

In the experimental disclosure which follows, the following abbreviations apply: Ab (antibody); AE (adverse event); DBPCFC (double-blind placebo-controlled oral food challenge); ELISA (enzyme-linked immunosorbent assay); IEMA (immunoenzymetric assay); IgE (immunoglobulin E); IU (international units); mAb (monoclonal antibody); OFC (oral food challenge); OIT (oral immunotherapy); OLE (open-label extension); QoL (quality of life), SOC (system organ classes); and TEAE (treatment-emergent AE).

Example 1

Treatment of Patients with Multiple Food Allergies with Omalizumab

This Example describes Screening, Stage 1, and Stage 1 Open-Label Extension (OLE) of a 3-stage Phase 3 clinical study (OUtMATCH) to test use of omalizumab for treatment of human subjects having allergies to one or more foods. Stage 1 is directed to use of omalizumab as a monotherapy to treat food allergy patients, i.e., without receiving oral immunotherapy and while practicing food avoidance. A flow chart of Stage 1 of the study design is shown in FIG. 1, which details the screening stage using oral food challenges, Stage 1 employing treatment and re-testing with oral food challenges and Stage 1 OLE employing continued treatment and re-testing with oral food challenges.

The study was open to children and adults (1 to 55 years of age) who are allergic to peanut and at least two other foods (selected from milk, egg, wheat, cashew, hazelnut, and walnut) to evaluate the ability of subjects to consume foods without dose-limiting symptoms (described below in Table 1-1) during a double-blind placebo-controlled food challenge (DBPCFC; Sampson, Ann Allergy, 60:262-269, 1988) after treatment with either omalizumab or placebo.

TABLE 1-1

Dose-limiting Symptoms

| Severity | Symptoms |
|---|---|
| Mild | Skin: limited or localized hives, swelling (e.g., mild lip edema), skin flushing (e.g., few areas of faint erythema) or mild pruritus (e.g., occasional scratching).<br>Respiratory: rhinorrhea (e.g., occasional sniffling or sneezing), nasal congestion, occasional cough, throat discomfort.<br>GI: mild abdominal discomfort (including mild nausea with or without decreased activity), isolated emesis thought to be secondary to gag. |
| Moderate | Skin: systemic hives (e.g., numerous or widespread hives), swelling (e.g., significant lip or face edema), pruritus causing protracted scratching, more than a few areas of erythema or pronounced erythema.<br>Respiratory: throat tightness without hoarseness, persistent cough ,wheezing without dyspnea.<br>GI: persistent moderate abdominal pain/cramping/nausea with decreased activity, vomiting. |
| Severe | Skin: severe generalized urticaria/angioedema/erythema.<br>Respiratory: laryngeal edema, throat tightness with hoarseness, wheezing with dyspnea, stridor.<br>GI: severe abdominal pain/cramping/repetitive vomiting.<br>Neurological: change in mental status.<br>Circulatory: clinically significant hypotension |

A summary of the Stage 1 study, Stage 1 study protocol, and Stage 1 study results of an interim analysis in 165 pediatric patients (age ≥1 year and <18 years of age) is described below.

Stage 1: Participants were those who experienced dose-limiting symptoms after receiving a single dose of ≤100 mg of peanut protein and ≤300 mg protein for each of the other two foods, or those who experienced no dose-limiting symptoms after receiving placebo at any single dose up to 300 mg protein during the Screening DBPCFC were randomized 2:1 to 16-20 weeks of treatment with omalizumab or placebo for omalizumab per the omalizumab dosing table of FIG. 2. After 16-20 weeks of treatment, each participant completed a DBPCFC consisting of placebo and each of their three specific foods to a cumulative dose of 6044 mg protein of each food.

Stage 1 Open-Label Extension (OLE): The first 60 participants who completed Stage 1 were selected to participate in the OLE. Each participant received 24-28 weeks of open label omalizumab. After 24-28 weeks of treatment in the OLE, each participant completed a DBPCFC consisting of placebo and each of their three specific foods to a cumulative dose of 8044 mg protein of each food.

Objectives

Primary objective: To compare the ability to consume foods without dose-limiting symptoms during a DBPCFC after treatment with either omalizumab or placebo for omalizumab.

Secondary objective: To evaluate safety during treatment with either omalizumab or placebo for omalizumab.

Exploratory objectives: To compare quality of life after treatment with either omalizumab or placebo for omalizumab. For the open label extension (OLE), to assess of the safety and efficacy of either 24 weeks (participants who received placebo prior to OLE) or 40 weeks (participants who received omalizumab prior to OLE) of treatment with omalizumab, and to assess quality of life at the end of either 24 or 40 weeks of treatment with omalizumab.

Pharmacokinetic objectives: To evaluate serum omalizumab concentrations during treatment with omalizumab. For the OLE, to assess serum omalizumab concentrations at the end of either 24 weeks (participants who received placebo prior to OLE) or 40 weeks (participants who received omalizumab prior to OLE) of treatment with omalizumab.

Biomarker objectives: To compare immunological responses after treatment with either omalizumab or placebo for omalizumab, and to determine whether immunological responses can be used to predict the ability to consume foods without dose-limiting systems during a DBPCFC after treatment with either omalizumab or placebo for omalizumab. For the OLE, to assess immunological responses at the end of either 24 or 40 weeks of treatment with omalizumab.

Endpoints

Primary endpoint: Consumption of a single dose of ≥600 mg of peanut protein without dose-limiting symptoms during the DBPCFC at the end of Stage 1. A participant who met this endpoint would be considered a "success" while a participant who did not meet this endpoint would be considered a "failure".

Key Secondary endpoints: Consumption of a single dose of ≥1000 mg of cashew protein without dose-limiting symptoms during the DBPCFC at the end of Stage 1; consumption of a single dose of ≥1000 mg of milk protein without dose-limiting symptoms during the DBPCFC at the end of Stage 1; and consumption of a single dose of ≥1000 mg of egg protein without dose-limiting symptoms during the DBPCFC at the end of Stage 1.

Other secondary endpoints: Consumption of a single dose of ≥600 mg, ≥1000 mg, ≥1 dose of 2000 mg, or 2 doses of 2000 mg protein of each food, at least two foods, or all three foods without dose-limiting symptoms during the DBPCFC at the end of Stage 1 (except for those endpoints already defined by the primary and key secondary endpoints in Stage 1); and number of foods consumed at a single dose of ≥600 mg, ≥1000 mg, ≥1 dose of 2000 mg, or 2 doses of 2000 mg protein of each food without dose-limiting symptoms during the DBPCFC at the end of Stage 1.

Safety endpoints: an adverse event related to study therapy regimen received during Stage 1 or received during Stage 1 OLE.

Exploratory endpoints: Percent change in the maximum dose of food protein consumed without dose-limiting symptoms during the DBPCFC at the end of Stage 1; consumption of a single dose of ≥600 mg, ≥1000 mg, ≥1 dose of 2000 mg, ≥2 doses of 2000 mg, or 3 doses of 2000 mg protein of each food, at least two foods, or all three foods without dose-limiting symptoms during the DBPCFC at the end of Stage 1 OLE; number of foods consumed at a single dose of ≥600 mg, ≥1000 mg, ≥1 dose of 2000 mg, ≥2 doses of 2000 mg, or 3 doses of 2000 mg protein of each food without dose-limiting symptoms during the DBPCFC at the end of Stage 1 OLE; and change in quality of life (QoL). QoL was assessed between Week 0 in Stage 1, at the first DBPCFC visit at the end of Stage 1, and for those participants who move to Stage 1 OLE, between Week 0 in Stage 1 and the first omalizumab injection visit in Stage 1 OLE, the first DBPCFC visit at the end of Stage 1 OLE, and the last DBPCFC visit at the end of Stage 1 OLE.

QOL was measured by the Food Allergy Quality of Life Questionnaire-Parent Form (FAQLQ-PF) for participants aged 0-12 years; Food Allergy Quality of Life Questionnaire—Child Form (FAQLQ-CF) for children/adolescents aged 8-12 years; Food Allergy Quality of Life Questionnaire-Teenager Form (FAQLQ-TF) for participants aged 13-17 years; and Food Allergy Quality of Life Questionnaire-Adult Form (FAQLQ-AF) (Flokstra-de Blok, B. M. J. (2014). Food Allergy Quality of Life Questionnaires (FAQLQ). In: Michalos, A. C. (eds) Encyclopedia of Quality of Life and Well-Being Research. Springer, Dordrecht) for participants aged 18 years and older.

Pharmacokinetic exploratory endpoints: Omalizumab trough concentration at the first Screening DBPCFC visit, the first DBPCFC visit at the end of Stage 1, and the first DBPCFC visit at the end of Stage 1 OLE for those participants who moved to Stage 1 OLE.

Biomarker exploratory endpoints: Total immunoglobulin E (IgE), total free IgE, allergen-specific IgE, allergen-specific immunoglobulin G4 (IgG4), allergen-specific immunoglobulin A (IgA), IgG4/IgE ratio, basophil activation, and skin prick tests (SPTs). Allergen-specific immune biomarkers (allergen-specific IgE, allergen-specific IgG4, allergen-specific IgA, basophil activation, and SPTs) were evaluated using peanut and the two other participant-specific foods. Immune biomarkers were analyzed at the following times: first Screening DBPCFC visit; first DBPCFC visit at the end of Stage 1; and first DBPCFC visit at the end of Stage 1 OLE (for those participants who move to Stage 1 OLE). Mechanistic exploratory endpoints, including dendritic cell and T cell assays, were measured at the following times: first Screening DBPCFC visit and first DBPCFC visit at the end of Stage 1.

ImmunoCAP™ Total IgE marketed by ThermoFisher Scientific was used to measure circulating IgE in serum and plasma (EDTA and heparin) samples according to the manufacturer's instructions, from participants prior to initiation of therapy with omalizumab or placebo. ImmunoCAP™ Total IgE is a quantitative enzyme linked immunosorbent assay, which measures circulating IgE within a range of 2 to 5000 kU/L (2 to 5000 IU/mL or about 2.4 ng/mL). A person having ordinary skill in the art can develop or use alternative assays, including ELISAs, to measure levels of human IgE in the serum or plasma of a subject.

Treatments

Omalizumab: Omalizumab is a recombinant humanized immunoglobulin G1 monoclonal antibody that binds to the $Fc_{\varepsilon}RI$ binding epitope of human IgE, preventing human IgE from binding to its specific high-affinity receptors on mast cells and basophils. Omalizumab is approved by the European Commission and US FDA for patients with moderate-severe asthma ≥6 years of age and for patients with chronic idiopathic urticaria ≥12 years of age. Omalizumab is not currently approved for treating food allergy in patients of any age.

Placebo for omalizumab: The composition of the placebo for omalizumab was the same as the composition of the active study drug without the omalizumab.

Omalizumab and placebo for omalizumab were administered as a subcutaneous injection according to the omalizumab dosing table of FIG. 2. Throughout Stage 1 and Stage 1 OLE, each participant and/or their parent/guardian were instructed to strictly avoid all foods to which they are allergic.

Patient Selection Criteria

Patient Selection Inclusion Criteria

- 1 year to less than 56 years of age at Screening.
- Peanut allergy and:
  1. Positive SPT (≥4 mm wheal greater than saline control) to peanut;
  2. Positive peanut IgE (≥6 kUA/L) at Screening or within three months of Screening, determined by ImmunoCap™; and
  3. Positive blinded oral food challenge (OFC) to peanut during the Screening DBPCFC, defined as experiencing dose-limiting symptoms (see Table 1-1) at a single dose of ≤100 mg of peanut protein.
- Allergic to at least two of six other foods (i.e., milk, egg, wheat, cashew, hazelnut, walnut; milk and egg allergy was defined as unable to tolerate both cooked and uncooked forms) and:
  1. Milk, egg, or wheat:
     - Positive SPT (≥4 mm wheal greater than saline control) to food;
     - Positive food specific IgE (≥6 kUA/L) at Screening or within three months of Screening, determined by ImmunoCap™; and.
     - Positive blinded OFC to food during the Screening DBPCFC, defined as experiencing dose-limiting symptoms (see Table 1-1) at a single dose of ≤300 mg of food protein.
  2. Cashew, hazelnut, or walnut:
     - Positive SPT (≥4 mm wheal greater than saline control) to food or positive food specific IgE (≥6 kUA/L) at Screening or within three months of Screening, determined by ImmunoCap™; and
     - Positive blinded OFC to food during the Screening DBPCFC, defined as experiencing dose-limiting symptoms (see Table 1-1) at a single dose of ≤300 mg of food protein.
- Body weight (as measured at Screening) and total serum IgE level (as measured within three months of Screening) suitable for omalizumab dosing.
- Was willing to be trained and provide an epinephrine autoinjector for the duration of the study.

Patient Selection Exclusion Criteria

- Clinically significant laboratory abnormalities at screening
- Dose-limiting symptoms to the blinded OFC to placebo during Screening DBPCFC.

Sensitivity or suspected or known allergy to any ingredients or excipients of the active or placebo OFC material, or drugs related to omalizumab.

Poorly controlled atopic dermatitis at screening.

Poorly controlled or severe asthma or wheezing at screening, such as at least one of:

1. Global Initiative for Asthma criteria regarding asthma control latest guidelines;
2. History of two or more systemic corticosteroid courses within six months of screening or one course of systemic corticosteroids within three months of screening to treat asthma or wheezing;
3. Prior intubation or mechanical ventilation for asthma or wheezing,
4. One hospitalization or emergency department visit for asthma or wheezing within six months of screening;
5. Forced expiratory volume in one second (FEV1) <80% of predicted or FEV1/forced vital capacity (FVC)<75%, with or without controller medications (only for participants who are aged seven years or older and are able to perform spirometry); and/or
6. Inhaled corticosteroid (ICS) dosing of >500 mcg daily fluticasone.

History of severe anaphylaxis to participant-specific foods.

Treatment with a burst of oral, intramuscular, or intravenous steroids of more than two days for an indication other than asthma or wheezing within 30 days of screening.

Currently receiving oral, IM, or IV corticosteroids, tricyclic antidepressants, or oral or topical β-blockers.

History of eosinophilic gastrointestinal disease within three years of screening.

History of cancer.

Previous adverse reaction to omalizumab.

History of any immunotherapy to any of the foods included in this study within six months of screening.

Treatment with monoclonal antibody therapy, or other immunomodulatory therapy within six months of screening.

In "build-up" phase of inhalant allergen immunotherapy.

Inability to discontinue antihistamines for the minimum washout-periods for SPTs or OFCs.

Participation in another therapeutic or interventional clinical study within 90 days of screening.

Use of investigational drugs within 24 weeks of screening.

Past or current medical problems, history of other chronic diseases requiring therapy, findings from physical assessment, or abnormalities in clinical laboratory testing, which may post additional risks, interfere with participation, or impact quality or interpretation of data.

Screening

Participants who met initial eligibility criteria underwent a double-blinded, placebo-controlled, food challenge (DBPCFC) according to the dosing schedule of Table 1-2. The DBPCFC consisted of four blinded oral food challenges (OFCs): three active OFCs (peanut and two additional foods) and one placebo OFC (oat). The DBPCFC was conducted in up to four separate visits. The food challenges were prepared from allergen food protein flours (active) and oat flour (placebo), respectively.

Food challenges were performed under medical supervision with emergency medications immediately available. The maximum cumulative dose for each blinded OFC during the Screening DBPCFC was 444 mg of protein. For the blinded OFC to peanut during the Screening DBPCFC, the maximum single dose given was 100 mg of peanut protein with the final single 300 mg dose consisting of placebo. For the additional blinded OFCs to two foods and the blinded OFC to placebo during the Screening DBPCFC, the maximum single dose given was 300 mg of the respective food protein/placebo.

After completing the Screening DBPCFC, participants who experienced dose-limiting symptoms to a single dose of ≤100 mg of peanut protein, ≤300 mg protein for each of the other two foods, and no dose-limiting symptoms during the blinded OFC to placebo moved to Stage 1.

TABLE 1-2

Dosing Schedule for DBPCFC Screening

| Dose # | Food Protein/Placebo (mg protein) | Cumulative Dose (mg protein) |
|---|---|---|
| 1 | 1 | 1 |
| 2 | 3 | 4 |
| 3 | 10 | 14 |
| 4 | 30 | 44 |
| 5 | 100 | 144 |
| 6[1] | 300 | 444 |

[1]During the blinded OFC to peanut, the 300 mg dose will be placebo so as not to surpass a maximum dose of 100 mg of peanut protein during the Screening DBPCFC and to preserve blinding.

Stage 1

Stage 1 assessed whether 16-20 weeks of treatment with omalizumab versus placebo for omalizumab would increase the proportion of participants who consumed each of the foods under study without dose-limiting symptoms, as assessed by a DBPCFC. Participants who experienced dose-limiting symptoms to a single dose of ≤100 mg of peanut protein, ≤300 mg protein for each of the other two foods, and no dose-limiting symptoms to placebo at any single dose up to 300 mg protein during the Screening DBPCFC were randomized 2:1 to 16-20 weeks of treatment with omalizumab or placebo for omalizumab per the dosing table provided in FIG. 2. This dosing table was specifically designed to accommodate the food allergy patient population characteristics (i.e., lower body weight and/or higher baseline total serum IgE level) of the OUtMATCH clinical trial.

During Stage 1, each participant (and/or a parent or guardian) was instructed to strictly avoid all foods to which they were allergic. Each randomized participant visited the clinic every two or four weeks, depending on assigned dosing frequency, for subcutaneous injection of omalizumab or placebo for omalizumab. Each participant was observed for at least two hours after the first three injections and for at least 30 minutes after all subsequent injections to assess for the development of adverse events (AEs).

After 16 weeks of treatment, each participant was subjected to a DBPCFC according to the dosing schedule of Table 1-3, consisting of placebo and each of their three specific foods to a cumulative dose of 6044 mg protein of each food. The DBPCFC took place within a maximum period of 28 days from the last treatment. Each participant who did not complete Stage 1 (i.e., does not complete all four blinded OFCs comprising the DBPCFC at the end of Stage 1) was withdrawn from the study and asked to attend an Early Discontinuation Visit. The first 60 participants who completed Stage 1 participated in the Stage 1 OLE.

TABLE 1-3

| Dosing Schedule for a DBPCFC at the End of Stage 1 and Stage 1 OLE | | |
|---|---|---|
| Dose # | Food Protein/Placebo (mg protein) | Cumulative Dose (mg protein) |
| 1 | 1 | 1 |
| 2 | 3 | 4 |
| 3 | 10 | 14 |
| 4 | 30 | 44 |
| 5 | 100 | 144 |
| 6 | 300 | 444 |
| 7 | 600 | 1044 |
| 8 | 1000 | 2044 |
| 9 | 2000 | 4044 |
| 10 | 2000 | 6044 |
| 11[1] | 2000 | 8044 |

[1]Dose 11 was only performed for the DBPCFC at the end of Stage 1 OLE.

Stage 1 OLE

Each participant received 24-28 weeks of open label omalizumab, before being subjected to a DBPCFC according to the dosing schedule of Table 1-3, consisting of placebo or each of their three specific foods to a cumulative dose of 8044 mg protein of each food. The DBPCFC took place within a maximum period of 28 days from the last treatment. Each participant who did not complete Stage 1 OLE (i.e., does not complete all four blinded OFCs comprising the DBPCFC at the end of OLE) was withdrawn from the study and asked to attend an Early Discontinuation Visit.

Interim Results

A preplanned interim analysis (IA) for efficacy was performed based on pre-specified thresholds for the primary and key secondary endpoints (p-value less than 0.0001 for peanut and less than 0.005 for each of cashew, milk and egg) that were agreed to by the United States Food and Drug Administration (USFDA). The interim analysis was conducted after the first 165 pediatric participants (ages 1 year to less than 18 years) either completed or discontinued Stage 1. A total of 92 pediatric males and 73 pediatric females (of which, 61 patients were aged 1 to less than 6 years of age and 104 patients aged 6 to less than 18 years) and 3 adult patients were included in the analysis. Patient weight ranged from approximately 10.1 kg to approximately 86.3 kg, with a mean and a median weight of approximately 30.7 kg and 25.5 kg, respectively.

Stage 1 of the study met pre-defined thresholds for significance for both primary and key secondary endpoints.

The interim results were reviewed by the Data Safety Monitoring Board, who recommended stopping Stage 1 with no further enrollment due to efficacy of omalizumab monotherapy. At the time the study was halted, 180 participants were enrolled, including 177 pediatric participants and 3 adult participants. Topline clinical study results from the interim analysis provide strong evidence that omalizumab reduces the risk of having an allergic reaction as a consequence of oral exposure to food allergens.

Both primary and key secondary endpoints (single dose of ≥600 mg of peanut and ≥1000 mg of cashew, milk, or egg protein, respectively) achieved pre-defined statistical significance based on the proportion of participants without dose-limiting symptoms during the Double-Blind Placebo-Controlled Food Challenge (DBPCFC) at the end of Stage 1. The safety profile between omalizumab-treated and placebo-treated participants was generally comparable.

Baseline demographics were generally balanced across treatment arms. The mean age across treatment arms was 7.8 years for the pediatric participants: 37% were <6 years of age, 37.6% were age 6 to <12 years, and 25.5% were age 12 to <18 years. Among the pediatric participants, 92 males (55.8%) and 73 females (44.2%) were enrolled. For the adult participants, 3 males with ages 18, 20, and 28 years were enrolled. Ninety seven percent of participants completed Stage 1.

Efficacy

At the Screening DBPCFC, all 165 participants had dose-limiting reaction to ≤100 mg of peanut protein, 94 participants had dose-limiting reaction to ≤100 mg of cashew, 67 participants had dose-limiting reaction to ≤100 mg of milk, and 55 participants had dose-limiting reaction to ≤100 mg of egg.

The study met the primary endpoint and achieved statistical significance on the proportion of participants who could consume a single dose of ≥600 mg of peanut protein without dose-limiting symptoms during the DBPCFC at the end of Stage 1. In the omalizumab-treated group, 68.2% of participants passed the DBPCFC compared to 5.5% in placebo (Δ: 62.7%, OR: 37.14, p<0.00001).

The study also met all the key secondary endpoints. For cashew, 42.2% in the omalizumab-treated group versus 3.3% in placebo passed the DBPCFC (Δ: 38.9%, OR: 21.16, p=0.00006), for milk 65.8% versus 10.5% passed (Δ: 55.3%, OR: 16.35, p=0.00008), and for egg 67.4% versus 0 passed (Δ:67.4%, OR: Infinity, p<0.00001).

TABLE 1-4

| Key Results from Interim Analysis | | | | |
|---|---|---|---|---|
| | Peanut (600 mg) (N = 165) | Cashew (1000 mg) (N = 94) | Milk (1000 mg) (N = 57) | Egg (1000 mg) (N = 65) |
| Omalizumab, n | 110 | 64 | 38 | 46 |
| Success n (%) | 75 (68.2%) | 27 (42.2%) | 25 (65.8%) | 31 (67.4%) |
| Failure n (%) | 35 (31.8%) | 37 (57.8%) | 13 (34.2%) | 15 (32.6%) |
| Placebo, n | 55 | 30 | 19 | 19 |
| Success n (%) | 3 (5.5%) | 1 (3.3%) | 2 (10.5%) | 0 (0%) |
| Failure n (%) | 52 (94.5%) | 29 (96.7%) | 17 (89.5%) | 19 (100%) |
| Difference | | | | |
| Omalizumab-Placebo | 0.627 | 0.389 | 0.553 | 0.674 |
| (95% CI) | (0.4956, 0.7260) | (0.1993, 0.5281) | (0.2886, 0.7310) | (0.4880, 0.8047) |

TABLE 1-4-continued

| Key Results from Interim Analysis | Peanut (600 mg) (N = 165) | Cashew (1000 mg) (N = 94) | Milk (1000 mg) (N = 57) | Egg (1000 mg) (N = 65) |
|---|---|---|---|---|
| Odds Ratio (OR) | | | | |
| Omalizumab/ Placebo | 37.143 | 21.162 | 16.346 | Infinity |
| 95% CI | (10.6286, 194.0379) | (3.0326, 895.6612) | (2.9818, 158.7890) | (10.1446, Infinity) |
| P-Value* | <0.00001 | 0.00006 | 0.00008 | <0.00001 |

*2-sided p-value from Fisher's exact test.

Key results are listed in Table 1-4. Data from the OLE further support that omalizumab treatment is associated with a higher probability of passing the DBPCFC at the end of treatment and that the response from omalizumab administration is durable. For peanut, 72.1% of participants had no dose-limiting symptoms with ≥600 mg of peanut protein at the end of the Stage 1 OLE. Among participants with allergy to the foods tested as key secondary endpoints, 55.6% had no dose-limiting symptoms with ≥1000 mg of cashew, 76.0% of participants had no dose-limiting symptoms with ≥1000 mg of milk, and 77.8% had no dose-limiting symptoms with ≥1000 mg of egg. Response rates were higher among participants who received omalizumab compared to participants who received placebo for omalizumab in the placebo-controlled part of Stage 1.

Results also showed efficacy in the ability of treated subjects to consume doses of multiple foods without experiencing dose-limiting symptoms. Participants in the omalizumab and placebo groups were compared for their ability to consume a single dose of ≥600 mg, a single dose ≥1000 mg, ≥1 dose of 2000 mg, or 2 doses of 2000 mg of at least 2 of their participant-specific tested foods without dose-limiting symptoms during the DBPCFC at the end of Stage 1. Minimal numbers (1 to 3) participants treated with placebo were able to achieve these endpoints compared to many in the omalizumab group; for example, 47/110 placebo participants were able to consume 2 doses of 2000 mg of at least 2 of the tested foods compared to 1/55 in the placebo group (Δ=0.409, 95% CI: 0.2980298, 0.5100510; p<0.00001).

Participants in the omalizumab and placebo for omalizumab groups were compared for their ability to consume a single dose of ≥600 mg, a single dose of ≥1000 mg, ≥1 dose of 2000 mg, or 2 doses of 2000 mg of all 3 foods tested without dose-limiting symptoms during the DBPCFC at the end of Stage 1. One participant treated with placebo was able to consume a single dose of ≥600 mg of all 3 foods compared to almost half (53/110) participants in the omalizumab group (Δ=0.445, 95% CI: 0.3197320, 0.5491549; p<0.00001). No participants treated with placebo were able to consume 2 doses of 2000 mg of all 3 foods tested without dose-limiting symptoms compared to 27/110 participants in the omalizumab group (Δ=0.245, 95% CI: 0.1614, 0.3367; p<0.00001).

Odds ratios were calculated comparing the consumption of a higher number of foods without dose-limiting symptoms during the DBPCFCs at the end of Stage 1 between participants in the omalizumab and placebo for omalizumab groups. Whether challenges were with a single dose of ≥600 mg of each food, ≥1000 mg of each food, ≥1 dose of 2000 mg of each food, or 2 doses of 2000 mg of each food, participants in the omalizumab group were able to consume more foods than participants in the placebo group. For challenges with single doses of ≥600 mg of each food, 48.2% (53/110) of participants were able to consume 3 foods without dose-limiting symptoms, whereas only 3.6% (2/55) of participants in the placebo group were able to do so; 89.1% (49/55) participants in the placebo group were not able to consume any foods at this dose without dose-limiting symptoms. The odds ratio comparing the omalizumab and placebo for omalizumab groups was 37.791 (95% CI: 14.2527253, 100.2025203; p<0.00001). Similar results were observed for all dose levels of food challenges.

In this study in patients with food allergy, omalizumab treatment led to a reduction in serum free IgE and an increase in serum total IgE levels, similar to observations of asthma patients treated with omalizumab. The mean total IgE concentration at baseline was 810 IU/mL. After repeated dosing every 2 or 4 weeks, with dosage and frequency according to the dosing table in FIG. 2, the mean pre-dose free IgE concentration at Week 16 was 10.0 IU/mL, representing an approximately 99% reduction. Table 1-5 below shows free IgE levels. Total IgE levels in serum increased about 2.4-fold due to the formation of omalizumab-IgE complexes, which have a longer half-life compared with free IgE.

TABLE 1-5

Total Serum IgE Levels

| Statistic | Omalizumab (N = 110) | Placebo (N = 55) | Overall (N = 165) |
|---|---|---|---|
| **Screening** | | | |
| N | 37 | 18 | 55 |
| Mean | 1960.1 | 1932.9 | 1951.2 |
| SD | 1402.0 | 1050.2 | 1287.5 |
| Median | 1548.8 | 1629.9 | 1548.8 |
| Minimum | 418.7 | 580.9 | 418.7 |
| Maximum | 6935.7 | 4128.5 | 6935.7 |
| **After Stage 1** | | | |
| N | 39 | 19 | 58 |
| Mean | 20.0 | 2324.7 | 775.0 |
| SD | 9.8 | 1242.7 | 1295.5 |
| Median | 20.4 | 2093.3 | 24.9 |
| Minimum | 5.2 | 479.2 | 5.2 |
| Maximum | 48.6 | 4888.4 | 4888.4 |
| **% Change from Screening to Stage 1** | | | |
| N | 35 | 18 | 53 |
| Mean | −98.6 | 42.2 | −50.8 |
| SD* | 1.1 | 63.7 | 76.5 |
| Median | −98.8 | 28.5 | −98.3 |
| Minimum | −99.7 | −35.1 | −99.7 |
| Maximum | −95.1 | 202.3 | 202.29 |

*SD = standard deviation

Safety

The safety profile between omalizumab-treated and placebo-treated participants was generally comparable. The proportion of patients reporting an adverse event (AE) was numerically higher in the placebo arm. The majority of AEs were non serious and Grade 1 or 2 in severity. The number of participants with AEs of special interest and serious AEs (SAEs) was low. There were no deaths in the study.

Further, there were no AEs related to the key risks for omalizumab treatment such as anaphylaxis, arterial thrombotic events, or malignancies. The observed AEs were consistent with the known safety profile of omalizumab treatment, and no adverse drug reactions were identified from the initial review of the safety data.

Stage 1 Adverse Events (AE)

In Stage 1, a majority of the participants (112 participants, 67.9%) experienced at least one treatment-emergent AE (TEAE) for a total of 346 TEAEs. In the omalizumab group, 69 (62.7%) participants experienced a combined total of 216 TEAEs. In the placebo group, 43 (78.2%) participants experienced 130 TEAEs.

The most common system organ classes (SOCs) in which TEAEs were experienced by ≥15% of the participants were: Infections and Infestations (45 participants, 27.3%); Immune System Disorders (42 participants, 25.5%); General disorders and administration site conditions (34 participants, 20.6%); and Respiratory, thoracic, and mediastinal disorders (27 participants, 16.4%).

The most frequently reported TEAEs with an incidence ≥3% of the participants in Stage 1 were: hypersensitivity (35 participants, 21.2%); injection site reaction (16 participants, 9.7%); coronavirus infection (11 participants, 6.7%); pyrexia (9 participants, 5.5%); upper respiratory tract infection (8 participants, 4.8%); viral infection, asthma, urticaria, and diarrhea (7 participants, 4.2%); vomiting and cough (6 participants, 3.6%); and gastroenteritis and atopic dermatitis (5 participants, 3.0%).

Twenty-four participants (21.9%) experienced a total of 43 AEs related to omalizumab treatment. Among these AEs, injection site reaction was the most commonly reported related AE (11 participants reported 20 AEs).

Four (2.4%) participants experienced a total of 4 SAEs. In the omalizumab group, 3 (2.7%) participants experienced 3 SAEs (liver function test increased, systemic inflammatory response syndrome, and infectious mononucleosis). In the placebo group, one (1.8%) participant experienced 1 SAE (hypersensitivity).

A majority of the participants experienced AEs of Grade 1-2 in severity (97 participants, 58.8%). Grade 3-4 severity AEs were experienced by 15 participants. Twelve participants (7.3%) experienced Grade 3 AEs and 3 participants (1.8%) experienced Grade 4 AEs. No grade 5 AEs were reported. One participant in the omalizumab group experienced one AE that led to treatment withdrawal. One participant in the omalizumab group experienced one AE of special interest (infectious mononucleosis).

Stage 1 OLE AEs

In the OLE, 42 (71.2%) participants experienced 126 TEAEs.

The most common SOCs in which TEAEs were experienced by ≥15% of the participants were: Infections and Infestations (17 participants, 28.8%); General disorders and administration site conditions (12 participants, 20.3%); Immune System Disorders (12 participants, 20.3%); and Respiratory, thoracic, and mediastinal disorders (9 participants, 15.3%)

The most frequently reported TEAEs experienced by ≥5 participants in the Stage 1 OLE were: hypersensitivity (9 participants, 15.3%) and injection site reaction (8 participants, 13.6%).

Sixteen participants (27.1%) experienced a total of 28 AEs related to omalizumab. Among these AEs, injection site reaction was the most commonly reported related AE (8 participants reported 12 AEs).

A majority of the participants experienced AEs of Grade 1-2 severity (40 participants, 67.8%). Grade 3 severity AEs were experienced by 2 participants (3.4%). No grade 4 or 5 AEs were reported. No SAEs, AEs leading to treatment withdrawal, or AE of special interest were reported.

Pharmacodynamics

Observed post-treatment free IgE generally fell within the target range, with a mean (±SD) of 24.5 (±11.9) ng/ml at Week 16 (Stage 1).

The present disclosure is described in detail in the above example(s), which are offered to illustrate the disclosure. The example(s) are not in any way intended to limit the scope of the disclosure unless otherwise indicated in the claims. The attached figures are meant to be considered as integral parts of the specification.

SEQUENCES

```
SEQ ID NO: 1
>Omalizumab-Heavy
  1 EVQLVESGGG LVQPGGSLRL SCAVSGYSIT SGYSWNWIRQ APGKGLEWVA
 51 SITYDGSTNY NPSVKGRITI SRDDSKNTFY LQMNSLRAED TAVYYCARGS
101 HYFGHWHFAV WGQGTLVTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKEN WYVDGVEVHN AKTKPREEQY
301 NSTYRVVSVL TVLHQDWLNG KEYKCKVSNK ALPAPIEKTI SKAKGQPREP
351 QVYTLPPSRE EMTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 X
wherein X can be lysine (K) or absent

SEQ ID NO: 2
>Omalizumab-Light
  1 DIQLTQSPSS LSASVGDRVT ITCRASQSVD YDGDSYMNWY QQKPGKAPKL
 51 LIYAASYLES GVPSRFSGSG SGTDFTLTIS SLQPEDFATY YCQQSHEDPY
101 TFGQGTKVEI KRTVAAPSVF IFPPSDEQLK SGTASVVCLL NNFYPREAKV
151 QWKVDNALQS GNSQESVTEQ DSKDSTYSLS STLTLSKADY EKHKVYACEV
201 THQGLSSPVT KSFNRGEC
```

-continued

| SEQUENCES |
|---|
| SEQ ID NO: 3<br>>Omalizumab-VH<br>1 EVQLVESGGG LVQPGGSLRL SCAVSGYSIT SGYSWNWIRQ APGKGLEWVA<br>51 SITYDGSTNY NPSVKGRITI SRDDSKNTFY LQMNSLRAED TAVYYCARGS<br>101 HYFGHWHFAV WGQG |
| SEQ ID NO: 4<br>>Omalizumab-VL<br>1 DIQLTQSPSS LSASVGDRVT ITCRASQSVD YDGDSYMNWY QQKPGKAPKL<br>51 LIYAASYLES GVPSRESGSG SGTDFTLTIS SLQPEDFATY YCQQSHEDPY<br>101 TFGQGTKVEI KRTV |
| SEQ ID NO: 5<br>>CDR-H1<br>GYSITSGY |
| SEQ ID NO: 6<br>>CDR-H2<br>TYDGS |
| SEQ ID NO: 7<br>>CDR-H3<br>GSHYFGHWHFAV |
| SEQ ID NO: 8<br>>CDR-L1<br>RASQSVDYDGDSYMN |
| SEQ ID NO: 9<br>>CDR-L2<br>AASYLES |
| SEQ ID NO: 10<br>>CDR-L3<br>QQSHEDPYT |

SEQUENCE LISTING

```
Sequence total quantity: 10
SEQ ID NO: 1            moltype = AA  length = 451
FEATURE                 Location/Qualifiers
source                  1..451
                        mol_type = protein
                        organism = synthetic construct
VARIANT                 451
                        note = X can be lysine (K) or absent
SEQUENCE: 1
EVQLVESGGG LVQPGGSLRL SCAVSGYSIT SGYSWNWIRQ APGKGLEWVA SITYDGSTNY  60
NPSVKGRITI SRDDSKNTFY LQMNSLRAED TAVYYCARGS HYFGHWHFAV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG X                                 451

SEQ ID NO: 2            moltype = AA  length = 218
FEATURE                 Location/Qualifiers
source                  1..218
                        mol_type = protein
                        organism = synthetic construct
SEQUENCE: 2
DIQLTQSPSS LSASVGDRVT ITCRASQSVD YDGDSYMNWY QQKPGKAPKL LIYAASYLES  60
GVPSRFSGSG SGTDFTLTIS SLQPEDFATY YCQQSHEDPY TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 3            moltype = AA  length = 114
FEATURE                 Location/Qualifiers
source                  1..114
                        mol_type = protein
                        organism = synthetic construct
```

-continued

```
SEQUENCE: 3
EVQLVESGGG LVQPGGSLRL SCAVSGYSIT SGYSWNWIRQ APGKGLEWVA SITYDGSTNY  60
NPSVKGRITI SRDDSKNTFY LQMNSLRAED TAVYYCARGS HYFGHWHFAV WGQG        114

SEQ ID NO: 4           moltype = AA  length = 114
FEATURE                Location/Qualifiers
source                 1..114
                       mol_type = protein
                       organism = synthetic construct
SEQUENCE: 4
DIQLTQSPSS LSASVGDRVT ITCRASQSVD YDGDSYMNWY QQKPGKAPKL LIYAASYLES  60
GVPSRFSGSG SGTDFTLTIS SLQPEDFATY YCQQSHEDPY TFGQGTKVEI KRTV        114

SEQ ID NO: 5           moltype = AA  length = 8
FEATURE                Location/Qualifiers
source                 1..8
                       mol_type = protein
                       organism = synthetic construct
SEQUENCE: 5
GYSITSGY                                                           8

SEQ ID NO: 6           moltype = AA  length = 5
FEATURE                Location/Qualifiers
source                 1..5
                       mol_type = protein
                       organism = synthetic construct
SEQUENCE: 6
TYDGS                                                              5

SEQ ID NO: 7           moltype = AA  length = 12
FEATURE                Location/Qualifiers
source                 1..12
                       mol_type = protein
                       organism = synthetic construct
SEQUENCE: 7
GSHYFGHWHF AV                                                      12

SEQ ID NO: 8           moltype = AA  length = 15
FEATURE                Location/Qualifiers
source                 1..15
                       mol_type = protein
                       organism = synthetic construct
SEQUENCE: 8
RASQSVDYDG DSYMN                                                   15

SEQ ID NO: 9           moltype = AA  length = 7
FEATURE                Location/Qualifiers
source                 1..7
                       mol_type = protein
                       organism = synthetic construct
SEQUENCE: 9
AASYLES                                                            7

SEQ ID NO: 10          moltype = AA  length = 9
FEATURE                Location/Qualifiers
source                 1..9
                       mol_type = protein
                       organism = synthetic construct
SEQUENCE: 10
QQSHEDPYT                                                          9
```

We claim:

1. A method of reducing an allergic reaction in a subject to a food allergen, the method comprising:

administering to the subject by subcutaneous injection a pharmaceutical composition comprising a dose of omalizumab, wherein body weight of the subject is greater than 15 kg and less than or equal to 20 kg, wherein total serum IgE level of the subject is determined prior to administration of a first dose of omalizumab and when the total serum IgE level of the subject is:

(i) greater than 100 IU/ml and less than or equal to 200 IU/ml, the pharmaceutical composition is administered once about every four weeks and the dose of omalizumab is 75 mg; or (ii) greater than 500 IU/ml and less than or equal to 600 IU/ml, the pharmaceutical composition is administered once about every four weeks and the dose of omalizumab is 225 mg; or (iii) greater than 600 IU/ml and less than or equal to 700 IU/ml, the pharmaceutical composition is administered once about every four weeks and the dose of omalizumab is 225 mg; or (iv) greater than 700 IU/ml and less than or equal to 800 IU/ml, the pharmaceutical composition is administered once about every two weeks and the dose of omalizumab is 150 mg; or (v) greater than 800 IU/ml and less than or equal to 900 IU/ml, the pharmaceutical composition is administered once about every two weeks and the dose of omalizumab is 150 mg; or (vi) greater than 1100 IU/ml and less than or equal to 1200 IU/ml, the pharmaceutical composition is administered once about every two weeks and the dose of omalizumab is 225 mg; or (vii) greater than 1200 IU/ml and less than or equal to 1300 IU/ml, the pharmaceutical composition is administered once about every two weeks and the dose of omalizumab is 225 mg, and wherein the method comprises reducing the severity of an allergic reaction in the subject to the food allergen or reducing the incidence of allergic reaction in the subject to the food allergen.

2. The method of claim 1, wherein when the total serum IgE level of the subject is:

(i) greater than 100 IU/ml and less than or equal to 200 IU/ml, the pharmaceutical composition is administered once about every four weeks and the dose of omalizumab is 75 mg.

3. The method of claim 1, wherein when the total serum IgE level of the subject is:

(ii) greater than 500 IU/ml and less than or equal to 600 IU/ml, the pharmaceutical composition is administered once about every four weeks and the dose of omalizumab is 225 mg.

4. The method of claim 1, wherein when the total serum IgE level of the subject is:

(iii) greater than 600 IU/ml and less than or equal to 700 IU/ml, the pharmaceutical composition is administered once about every four weeks and the dose of omalizumab is 225 mg.

5. The method of claim 1, wherein when the total serum IgE level of the subject is:

(iv) greater than 700 IU/ml and less than or equal to 800 IU/ml, the pharmaceutical composition is administered once about every two weeks and the dose of omalizumab is 150 mg.

6. The method of claim 1, wherein when the total serum IgE level of the subject is:

(v) greater than 800 IU/ml and less than or equal to 900 IU/ml, the pharmaceutical composition is administered once about every two weeks and the dose of omalizumab is 150 mg.

7. The method of claim 1, wherein when the total serum IgE level of the subject is:

(vi) greater than 1100 IU/ml and less than or equal to 1200 IU/ml, the pharmaceutical composition is administered once about every two weeks and the dose of omalizumab is 225 mg.

8. The method of claim 1, wherein when the total serum IgE level of the subject is:

(vii) greater than 1200 IU/ml and less than or equal to 1300 IU/ml, the pharmaceutical composition is administered once about every two weeks and the dose of omalizumab is 225 mg.

9. The method of claim 1, wherein the subject has a food allergy to one or more food allergens selected from the group consisting of peanut, milk, egg, wheat, cashew, hazelnut, and walnut protein.

10. The method of claim 1, wherein the subject is 1 year of age or older and/or less than 6 years of age.

11. The method of claim 1, wherein the subject has asthma.

12. The method of claim 1, wherein the subject does not have asthma.

13. The method of claim 1, wherein the body weight of the subject is determined prior to administration of the pharmaceutical compound.

14. The method of claim 1, wherein the method does not comprise concurrent oral immunotherapy.

15. The method of claim 1, wherein the method is practiced by the subject in conjunction with food allergen avoidance.

16. The method of claim 1, wherein the pharmaceutical composition is administered once about every two weeks and the dose of omalizumab is:

150 mg when the total serum IgE level of the subject is greater than 700 IU/ml and less than or equal to 800 IU/ml; or 150 mg when the total serum IgE level of the subject is greater than 800 IU/ml and less than or equal to 900 IU/ml; or 225 mg when the total serum IgE level of the subject is greater than 1100 IU/ml and less than or equal to 1200 IU/ml; or 225 mg when the total serum IgE level of the subject is greater than 1200 IU/ml and less than or equal to 1300 IU/ml.

17. The method of claim 16, wherein the subject has a food allergy to one or more food allergens selected from the group consisting of peanut, milk, egg, wheat, cashew, hazelnut, and walnut protein.

18. The method of claim 16, wherein the subject is 1 year of age or older and/or less than 6 years of age.

19. The method of claim 16, wherein the subject has asthma.

20. The method of claim 16, wherein the subject does not have asthma.

21. The method of claim 16, wherein the body weight of the subject is determined prior to administration of the pharmaceutical compound.

22. The method of claim 16, wherein the method does not comprise concurrent oral immunotherapy.

23. The method of claim 1, wherein the pharmaceutical composition is administered once about every four weeks and the dose of omalizumab is:

75 mg when the total serum IgE level of the subject is greater than 100 IU/ml and less than or equal to 200 IU/ml; or 225 mg when the total serum IgE level of the subject is greater than 500 IU/ml and less than or equal to 600 IU/ml; or 225 mg when the total serum IgE level of the subject is greater than 600 IU/ml and less than or equal to 700 IU/ml.

24. The method of claim 23, wherein the subject has a food allergy to one or more food allergens selected from the group consisting of peanut, milk, egg, wheat, cashew, hazelnut, and walnut protein.

25. The method of claim 23, wherein the subject is 1 year of age or older and/or less than 6 years of age.

26. The method of claim 23, wherein the subject has asthma.

27. The method of claim 23, wherein the subject does not have asthma.

28. The method of claim 23, wherein the body weight of the subject is determined prior to administration of the pharmaceutical compound.

29. The method of claim 23, wherein the method does not comprise concurrent oral immunotherapy.

* * * * *